(12) United States Patent
Walker et al.

(10) Patent No.: US 11,092,549 B2
(45) Date of Patent: Aug. 17, 2021

(54) FLUORESCENT PROBES FOR DRUG PERMEABILITY IN GRAM NEGATIVE BACTERIA

(71) Applicants: Saint Louis University, St. Louis, MO (US); The Board of Regents of the University of Oklahoma, Norman, OK (US)

(72) Inventors: John K. Walker, St. Louis, MO (US); Keith Haynes, St. Louis, MO (US); Narges Abdali, Norman, OK (US); Valentin V. Rybenkov, Norman, OK (US); Helen I. Zgurskaya, Norman, OK (US)

(73) Assignees: Saint Louis University, St. Louis, MO (US); The Board of Regents of the University of Oklahoma, Norman, OK (US)

( * ) Notice: Subject to any disclaimer, the term of this patent is extended or adjusted under 35 U.S.C. 154(b) by 240 days.

(21) Appl. No.: 16/419,492

(22) Filed: May 22, 2019

(65) Prior Publication Data
US 2020/0018705 A1  Jan. 16, 2020

Related U.S. Application Data

(60) Provisional application No. 62/675,482, filed on May 23, 2018.

(51) Int. Cl.
*G01N 21/64* (2006.01)
*C12Q 1/04* (2006.01)
*C07D 401/04* (2006.01)

(52) U.S. Cl.
CPC ....... *G01N 21/6486* (2013.01); *C07D 401/04* (2013.01); *C12Q 1/04* (2013.01); *G01N 21/6408* (2013.01); *G01N 21/6428* (2013.01)

(58) Field of Classification Search
CPC .......... G01N 21/6486; G01N 21/6408; G01N 21/6428; C07D 401/04; C12C 1/04
See application file for complete search history.

(56) References Cited

PUBLICATIONS

Abdali, Narges, et al. "Reviving antibiotics: efflux pump inhibitors that interact with AcrA, a membrane infusion protein of the AcrAB-TOIC multidrug efflux pump." ACS infectious diseases 3.1 (2016):89-98. (Year: 2016).*
Abdali, Narges, et al. "Reviving antibiotics: efflux pump inhibitors that interact with AcrA, a membrane fusion protein of the AcrAB-ToIC multidrug efflux pump." *ACS injectious diseases* 3.1 (2016): 89-98.
Fange David, et al. "Drug efflux pump deficiency and drug targetresistance masking in growing bacteria." *PNaS 106.20* (2009): 8215-8220.
Haynes, Keith M., et al. "Identification and Structure—Activity Relationships of Novel Compounds that Potentiate the Activities of Antibiotics in *Escherichia coli.*" *Journal of medicinal chemistry* 60.14 (2017): 6205-6219.

(Continued)

*Primary Examiner* — Lyle Alexander
*Assistant Examiner* — Kathryn Elizabeth Limbaugh
(74) *Attorney, Agent, or Firm* — Parker Highlander PLLC

(57) ABSTRACT

Described are compounds and methods useful in measuring membrane permeability and efflux transporter activity in bacteria, including multidrug resistance Gram negative bacteria.

21 Claims, 3 Drawing Sheets

(56) References Cited

PUBLICATIONS

Li, Xian-Zhi, Keith Poole, and Hiroshi Nikaido. "Contributions of MexAB-OprM and an EmrE homolog to intrinsic resistance of Pseudomonas aeruginosa to aminoglycosides and dyes." *Antimicrobial agents and chemotherapy* 47.1 (2003): 27-33.

Li, Xian-Zhi, Li and Keith Poole. "Interplay between the MexA-MexB-OprM multidrug efflux system and the outer membrane banter in the multiple antibiotic resistance of Pseudomonas aeruginosa." *Journal of Antimicrobial Chemotherapy* 45.4 (2000): 433-436.

Lomovskaya, Olga, et al. "Identification and characterization of inhibitors of multidrug resistance efflux pumps in Pseudomonas aeruginosa: novel agents for combination therapy." *Antimicrobial agents and chemotherapy* 45.1 (2001): 105-116.

Lomovskaya, Olga, et al. "Use of a genetic approach to evaluate the consequences of inhibition of efflux pumps in Pseudomonas aeruginosa." *Antimicrobial Agents and Chemotherapy* 43.6 (1999): 1340-1346.

Lovmar, Martin, et al, "Erythromycin resistance by L4/L22 mutations and resistance masking by drug efflux pump deficiency." *The EMBO journal* 28.6 (2009): 736-744.

Oethinger, Margret, et al. "Ineffectiveness of topoisomerase mutations in mediating clinically significant fluoroquinolone resistance in *Escheriehia coli* in the absence of the AcrAB efflux pump." *Antimicrobial Agents and Chemotherapy* 44.1 (2000): 10-13.

Sjuts Hanno, et al. "Molecular basis for inhibition of AcrB multidrug efflux pump by novel and powerful pyranopyridine derivatives." *PNaS* 113.13 (2016): 3509-3514.

Vargiu, Attilio V., et al. "Molecular mechanism of MBX2319 inhibition of *Escherichia coli* AcrB multidrug efflux pump and comparison with other inhibitors." *Antimicrobial agents and chemotherapy* 58.10 (2014): 6224-6234.

* cited by examiner

FIGS. 2A-C

FLUORESCENT PROBES FOR DRUG PERMEABILITY IN GRAM NEGATIVE BACTERIA

PRIORITY CLAIM

This application claims benefit of priority to U.S. Provisional Application Ser. No. 62/675,482, filed May 23, 2018, the entire contents of which are hereby incorporated by reference.

STATEMENT REGARDING FEDERAL FUNDING

This invention was made with government support under grant number 2R01AI052293-11AI awarded by the National Institutes of Health. The government has certain rights in the invention.

BACKGROUND

1. Field

The disclosure relates to the fields of microbiology, medicine and membrane biology. In particular, the disclosure relates to probes for use in assessing bacterial efflux pump activity in Gram negative bacteria.

2. Related Art

Multiple drug resistance (MDR), multidrug resistance or multiresistance is antimicrobial resistance shown by a species of microorganism to multiple antimicrobial drugs. The types most threatening to public health are MDR bacteria that resist multiple antibiotics; other types include MDR viruses, fungi, and parasites (resistant to multiple antifungal, antiviral, and antiparasitic drugs of a wide chemical variety). Recognizing different degrees of MDR, the terms extensively drug resistant (XDR) and pandrug-resistant (PDR) have been introduced.

Microorganisms have survived for thousands of years by their ability to adapt to antimicrobial agents. They do so via spontaneous mutation or by DNA transfer. This process enables some bacteria to oppose the action of certain antibiotics, rendering the antibiotics ineffective. These microorganisms employ several mechanisms in attaining multidrug resistance, including no longer relying on a glycoprotein cell wall, enzymatic deactivation of antibiotics, decreased cell wall permeability to antibiotics, altered target sites of antibiotic, increased mutation rate as a stress response, and efflux mechanisms to remove antibiotics As a result of these processes, many different bacteria now exhibit multi-drug resistance, including staphylococci, enterococci, gonococci, streptococci, enterobacteria, as well as numerous other gram-negative bacteria, and *Mycobacterium tuberculosis*. Antibiotic resistant bacteria are able to transfer copies of DNA that code for a mechanism of resistance to other bacteria even distantly related to them, which then are also able to pass on the resistance genes such that generations of antibiotics resistant bacteria are produced. This process is called horizontal gene transfer and presents a major challenge to treatment of infectious disease. Assays to assess the bacterial function associated with multidrug resistance are therefore highly valuable.

SUMMARY

Thus, the present disclosure provides methods for using compounds as fluorescent reporters of active efflux or cell permeation.

As described herein, the present disclosure provides compounds that have intrinsic environment-sensitive fluorescence. These compounds may be almost non-fluorescent in water solution but the fluorescence is enhanced inside bacterial cells through binding to membranes or nucleic acids and proteins of these cells. These compounds may also be used as substrates for multidrug efflux pumps. Without wishing to be bound by any theory, it is believed that when active efflux pumps are inactivated either through genetic modifications or synthetic inhibitors, these compounds are able to accumulate inside the cell to higher concentrations and give a fluorescent signal. The compounds described herein may be used as chemical probes to assess the range of physicochemical properties that are affected by active efflux and help govern permeation across the membrane in a different degree. This set of compounds may be used to create a measuring tool of cell envelope permeabilities. A set of such compounds may be used to evaluate permeability barriers in different bacterial strains including clinical multidrug resistant isolates. These methods described herein may also be extended to other cellular systems, such as yeast or human cells that use efflux pumps to limit intracellular concentrations of exogenous toxins. Some potential benefits may include mechanism-based diagnostics and optimization of chemotherapeutic treatments.

In one aspect, the present disclosure provides methods of determining permeability of a cellular membrane comprising:
(a) contacting a cell with a compound having the structure:

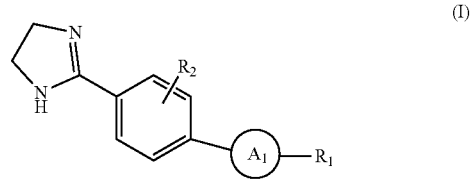

(I)

wherein:
  $A_1$ is arenediyl$_{(C \leq 12)}$, heteroarenediyl$_{(C \leq 12)}$, heterocycloalkanediyl$_{(C \leq 12)}$, or a substituted version of these groups, or —NR$_3$C(O)Y$_1$—; wherein:
    $R_3$ is hydrogen, alkyl$_{(C \leq 6)}$, or substituted alkyl$_{(C \leq 6)}$;
    $Y_1$ is a covalent bond, alkanediyl$_{(C \leq 12)}$, alkenediyl$_{(C \leq 12)}$, arenediyl$_{(C \leq 12)}$, heteroarenediyl$_{(C \leq 12)}$, or a substituted version of any of these groups;
  $R_1$ is aryl$_{(C \leq 18)}$, substituted aryl$_{(C \leq 18)}$, heteroaryl$_{(C \leq 18)}$, or substituted heteroaryl$_{(C \leq 18)}$; and
  $R_2$ is hydrogen, amino, cyano, halo, hydroxy, or alkyl$_{(C \leq 8)}$, aryl$_{(C \leq 8)}$, aralkyl$_{(C \leq 8)}$, acyl$_{(C \leq 8)}$, alkoxy$_{(C \leq 8)}$, heteroaryl$_{(C \leq 12)}$, heterocycloalkyl$_{(C \leq 12)}$, alkylamino$_{(C \leq 8)}$, dialkylamino$_{(C \leq 8)}$, or a substituted version of any of these groups; or
a compound of the formula:

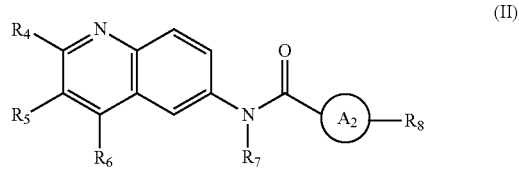

(II)

wherein:
A$_2$ is covalent bond, alkenediyl$_{(C \leq 12)}$, or substituted alkenediyl$_{(C \leq 12)}$;
R$_4$ and R$_5$ are each independently hydrogen, alkyl$_{(C \leq 8)}$, or substituted alkyl$_{(C \leq 8)}$;
R$_6$ is hydrogen, hydroxy, or amino; or alkoxy$_{(C \leq 8)}$, acyloxy$_{(C \leq 8)}$, alkylamino$_{(C \leq 8)}$, dialkylamino$_{(C \leq 8)}$, or a substituted version of any of these groups;
R$_7$ is hydrogen, alkyl$_{(C \leq 6)}$, or substituted alkyl$_{(C \leq 6)}$; and
R$_8$ is aryl$_{(C \leq 18)}$, substituted aryl$_{(C \leq 18)}$, heteroaryl$_{(C \leq 18)}$, substituted heteroaryl$_{(C \leq 18)}$; or a pharmaceutically acceptable salt thereof.

(b) incubating said cell for sufficient time to permit uptake of said compound by said cell;
(c) measuring a change fluorescent signal as compared to said cell prior to step (a),
wherein the change in fluorescent signal is a measure of membrane permeability.

In some embodiments, the compound is further defined as:

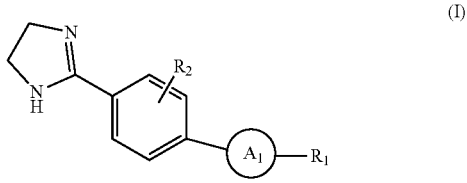

(I)

wherein:
A$_1$ is arenediyl$_{(C \leq 12)}$, heteroarenediyl$_{(C \leq 12)}$, heterocycloalkanediyl$_{(C \leq 12)}$, or a substituted version of these groups, or —NR$_3$C(O)Y$_1$—; wherein:
R$_3$ is hydrogen, alkyl$_{(C \leq 6)}$, or substituted alkyl$_{(C \leq 6)}$;
Y$_1$ is a covalent bond, alkanediyl$_{(C \leq 12)}$, alkenediyl$_{(C \leq 12)}$, arenediyl$_{(C \leq 12)}$, heteroarenediyl$_{(C \leq 12)}$, or a substituted version of any of these groups;
R$_1$ is aryl$_{(C \leq 18)}$, substituted aryl$_{(C \leq 18)}$, heteroaryl$_{(C \leq 18)}$, or substituted heteroaryl$_{(C \leq 18)}$; and
R$_2$ is hydrogen, amino, cyano, halo, hydroxy, or alkyl$_{(C \leq 8)}$, aryl$_{(C \leq 8)}$, aralkyl$_{(C \leq 8)}$, acyl$_{(C \leq 8)}$, alkoxy$_{(C \leq 8)}$, heteroaryl$_{(C \leq 12)}$, heterocycloalkyl$_{(C \leq 12)}$, alkylamino$_{(C \leq 8)}$, dialkylamino$_{(C \leq 8)}$, or a substituted version of any of these groups;
or a pharmaceutically acceptable salt thereof.

In some embodiments, said compound is further defined as:

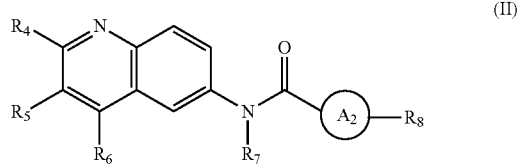

(II)

wherein:
A$_2$ is covalent bond, alkenediyl$_{(C \leq 12)}$, or substituted alkenediyl$_{(C \leq 12)}$;
R$_4$ and R$_5$ are each independently hydrogen, alkyl$_{(C \leq 8)}$, or substituted alkyl$_{(C \leq 8)}$;
R$_6$ is hydrogen, hydroxy, or amino; or alkoxy$_{(C \leq 8)}$, acyloxy$_{(C \leq 8)}$, alkylamino$_{(C \leq 8)}$, dialkylamino$_{(C \leq 8)}$, or a substituted version of any of these groups;
R$_7$ is hydrogen, alkyl$_{(C \leq 6)}$, or substituted alkyl$_{(C \leq 6)}$; and
R$_8$ is aryl$_{(C \leq 18)}$, substituted aryl$_{(C \leq 18)}$, heteroaryl$_{(C \leq 18)}$, substituted heteroaryl$_{(C \leq 18)}$;
or a pharmaceutically acceptable salt thereof.

In some embodiments, said compound is further defined as:

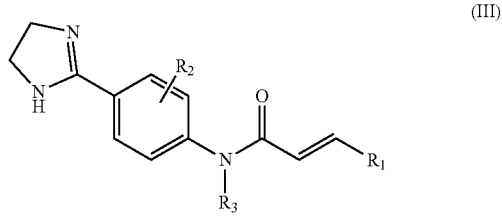

(III)

wherein:
R$_1$ is aryl$_{(C \leq 18)}$, substituted aryl$_{(C \leq 18)}$, heteroaryl$_{(C \leq 18)}$, or substituted heteroaryl$_{(C \leq 18)}$;
R$_2$ is hydrogen, amino, cyano, halo, hydroxy, or alkyl$_{(C \leq 8)}$, aryl$_{(C \leq 8)}$, aralkyl$_{(C \leq 8)}$, acyl$_{(C \leq 8)}$, alkoxy$_{(C \leq 8)}$, alkylamino$_{(C \leq 8)}$, dialkylamino$_{(C \leq 8)}$, or a substituted version of any of these groups; and
R$_3$ is hydrogen, alkyl$_{(C \leq 6)}$, or substituted alkyl$_{(C \leq 6)}$;
or a pharmaceutically acceptable salt thereof.

In some embodiments, R$_2$ is hydrogen. In some embodiments, R$_3$ is hydrogen. In some embodiments, the compound is further defined as:

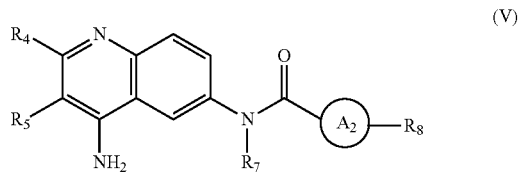

(V)

wherein:
A$_2$ is covalent bond, alkenediyl$_{(C \leq 12)}$, or substituted alkenediyl$_{(C \leq 12)}$;
R$_4$ and R$_5$ are each independently hydrogen, alkyl$_{(C \leq 8)}$, or substituted alkyl$_{(C \leq 8)}$;
R$_7$ is hydrogen, alkyl$_{(C \leq 6)}$, or substituted alkyl$_{(C \leq 6)}$; and
R$_8$ is aryl$_{(C \leq 1)}$, substituted aryl$_{(C \leq 18)}$, heteroaryl$_{(C \leq 18)}$, substituted heteroaryl$_{(C \leq 18)}$;
or a pharmaceutically acceptable salt thereof.

In some embodiments, the methods further comprise quantitating the change in fluorescent signal. In some embodiments, the fluorescent signal is quantitated by fluorescence microscopy. In other embodiments, the fluorescent signal is quantitated by fluorometer.

In some embodiments, said cell is a bacterial cell. In some embodiments, said cell is a Gram-negative bacterial cell such as *Escherichia coli*, *Pseudomonas aeruginosa*, *Acinetobacter baumannii*, *Klebsiella* species, *Burkholderia* species, *Enterobacter* species or *Stenotrophomonas maltophilia*. In some embodiments, said bacterial cell is multidrug resistant. In other embodiments, said cell is a fungal cell such as a *Candida* species, *Saccharomyces* species, or *Aspergillus* species. In some embodiments, said cell is a cancer cell. In some embodiments, the methods further comprise performing steps (b)-(c) in the presence of a candidate substance suspected of having membrane permeabilization activity. In some embodiments, step (c) is performed at multiple time points following step (b).

In yet another aspect, the present disclosure provides methods of determining efflux transport activity of a cellular membrane comprising:

(a) contacting a cell with a compound of the formula:

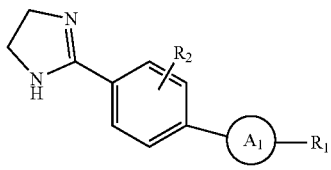

(I)

wherein:
- A is arenediyl$_{(C\leq12)}$, heteroarenediyl$_{(C\leq12)}$, heterocycloalkanediyl$_{(C\leq12)}$, or a substituted version of these groups, or —NR$_3$C(O)Y$_1$—; wherein:
  - R$_3$ is hydrogen, alkyl$_{(C\leq6)}$, or substituted alkyl$_{(C\leq6)}$;
  - Y$_1$ is a covalent bond, alkanediyl$_{(C\leq12)}$, alkenediyl$_{(C\leq12)}$, arenediyl$_{(C\leq12)}$, heteroarenediyl$_{(C\leq12)}$, or a substituted version of any of these groups;
- R$_1$ is aryl$_{(C\leq18)}$, substituted aryl$_{(C\leq18)}$, heteroaryl$_{(C\leq18)}$, or substituted heteroaryl$_{(C\leq18)}$; and
- R$_2$ is hydrogen, amino, cyano, halo, hydroxy, or alkyl$_{(C\leq8)}$, aryl$_{(C\leq8)}$, aralkyl$_{(C\leq8)}$, acyl$_{(C\leq8)}$, alkoxy$_{(C\leq8)}$, heteroaryl$_{(C\leq12)}$, heterocycloalkyl$_{(C\leq12)}$, alkylamino$_{(C\leq8)}$, dialkylamino$_{(C\leq8)}$, or a substituted version of any of these groups; or a compound of the formula:

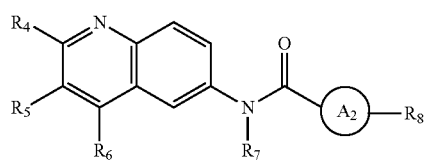

(II)

wherein:
- A$_2$ is covalent bond, alkenediyl$_{(C\leq12)}$, or substituted alkenediyl$_{(C\leq12)}$;
- R$_4$ and R$_5$ are each independently hydrogen, alkyl$_{(C\leq8)}$, or substituted alkyl$_{(C\leq8)}$;
- R$_6$ is hydrogen, hydroxy, or amino; or alkoxy$_{(C\leq8)}$, acyloxy$_{(C\leq8)}$, alkylamino$_{(C\leq8)}$, dialkylamino$_{(C\leq8)}$, or a substituted version of any of these groups;
- R$_7$ is hydrogen, alkyl$_{(C\leq6)}$, or substituted alkyl$_{(C\leq6)}$; and
- R$_8$ is aryl$_{(C\leq18)}$, substituted aryl$_{(C\leq18)}$, heteroaryl$_{(C\leq18)}$, substituted heteroaryl$_{(C\leq18)}$;

or a pharmaceutically acceptable salt thereof.

(b) incubating said cell for sufficient time to permit uptake of said compound by said cell;
(c) measuring a fluorescent signal in said cell; and
(d) measuring a change fluorescent signal in said cell as compared to step (c),
wherein the change in fluorescent signal is a measure of efflux transport activity.

In some embodiments, said compound is further defined as:

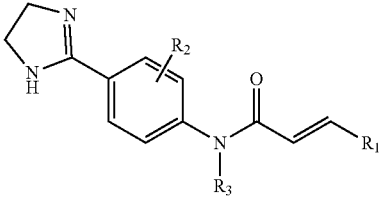

(III)

wherein:
- R$_1$ is aryl$_{(C\leq18)}$, substituted aryl$_{(C\leq18)}$, heteroaryl$_{(C\leq18)}$, or substituted heteroaryl$_{(C\leq18)}$;
- R$_2$ is hydrogen, amino, cyano, halo, hydroxy, and
- R$_3$ is hydrogen, alkyl$_{(C\leq6)}$, or substituted alkyl$_{(C\leq6)}$;

or a pharmaceutically acceptable salt thereof.

In some embodiments, R$_2$ is hydrogen. In some embodiments, R$_3$ is hydrogen. In some embodiments, the methods further comprise quantitating the change in fluorescent signal. In some embodiments, the fluorescent signal is quantitated by fluorescence microscopy. In other embodiments, the fluorescent signal is quantitated by fluorometer.

In some embodiments, said cell is a bacterial cell. In some embodiments, said cell is a Gram-negative bacterial cell such as *Escherichia coli*, *Pseudomonas aeruginosa*, *Acinetobacter baumannii*, *Klebsiella* species, *Burkholderia* species, *Enterobacter* species or *Stenotrophomonas maltophilia*. In some embodiments, said bacterial cell is multidrug resistant. In other embodiments, said cell is a fungal cell such as a *Candida* species, *Saccharomyces* species, or *Aspergillus* species. In some embodiments, said cell is a cancer cell. In some embodiments, the methods further comprise performing steps (b)-(d) in the presence of a candidate substance suspected of having membrane efflux transport inhibitory activity. In some embodiments, step (d) is performed at multiple time points following step (b).

In still yet another aspect, the present disclosure provides compounds of the formula:

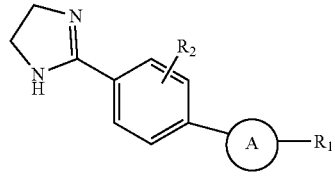

(I)

wherein:
- A is arenediyl$_{(C\leq12)}$, heteroarenediyl$_{(C\leq12)}$, heterocycloalkanediyl$_{(C\leq12)}$, or a substituted version of these groups, or —NR$_3$C(O)Y$_1$—; wherein:
  - R$_3$ is hydrogen, alkyl$_{(C\leq6)}$, or substituted alkyl$_{(C\leq6)}$;
  - Y$_1$ is a covalent bond, alkanediyl$_{(C\leq12)}$, alkenediyl$_{(C\leq12)}$, arenediyl$_{(C\leq12)}$, heteroarenediyl$_{(C\leq12)}$, or a substituted version of any of these groups;
- R$_1$ is aryl$_{(C\leq18)}$, substituted aryl$_{(C\leq18)}$, heteroaryl$_{(C\leq18)}$, or substituted heteroaryl$_{(C\leq18)}$; and
- R$_2$ is hydrogen, amino, cyano, halo, hydroxy, or alkyl$_{(C\leq8)}$, aryl$_{(C\leq8)}$, aralkyl$_{(C\leq8)}$, acyl$_{(C\leq8)}$, alkoxy$_{(C\leq8)}$, heteroaryl$_{(C\leq12)}$, heterocycloalkyl$_{(C\leq12)}$, alkylamino$_{(C≤8)}$, dialkylamino$_{(C≤8)}$, or a substituted version of any of these groups; or
a compound of the formula:

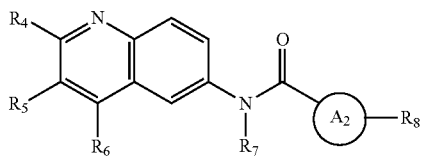
(II)

wherein:
  A$_2$ is covalent bond, alkenediyl$_{(C≤12)}$, or substituted alkenediyl$_{(C≤12)}$;
  R$_4$ and R$_5$ are each independently hydrogen, alkyl$_{(C≤8)}$, or substituted alkyl$_{(C≤8)}$;
  R$_6$ is hydrogen, hydroxy, or amino; or alkoxy$_{(C≤8)}$, acyloxy$_{(C≤8)}$, alkylamino$_{(C≤8)}$, dialkylamino$_{(C≤8)}$, or a substituted version of any of these groups;
  R$_7$ is hydrogen, alkyl$_{(C≤6)}$, or substituted alkyl$_{(C≤6)}$; and
  R$_8$ is aryl$_{(C≤1)}$, substituted aryl$_{(C≤18)}$, heteroaryl$_{(C≤18)}$, substituted heteroaryl$_{(C≤18)}$;
or a pharmaceutically acceptable salt thereof.

In some embodiments, A$_1$ is —NR$_3$C(O)CH=CH—. In some embodiments, R$_3$ is hydrogen. In some embodiments, R$_2$ is hydrogen. In some embodiments, R$_1$ is aryl$_{(C≤18)}$ or substituted aryl$_{(C≤18)}$. In some embodiments, R$_1$ is substituted aryl$_{(C≤18)}$. In some embodiments, the compounds are further defined as:

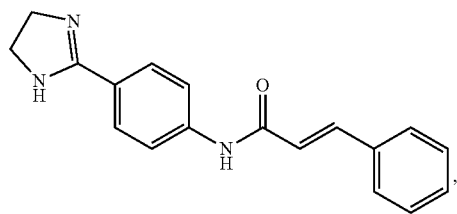
,

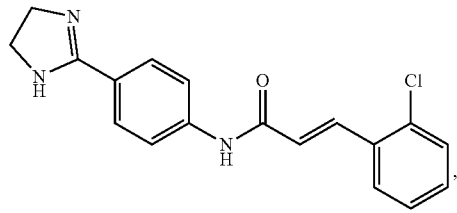
,

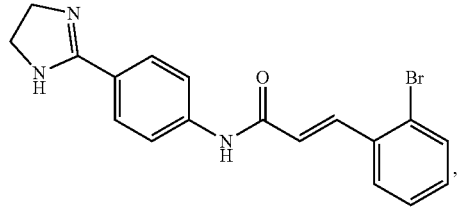
,

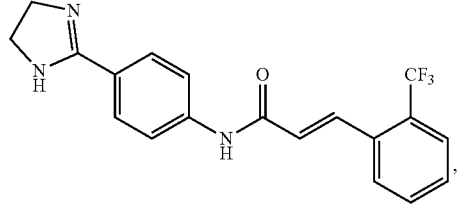
,

-continued

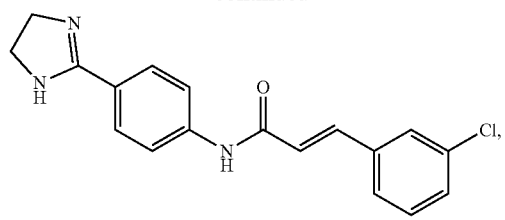
,

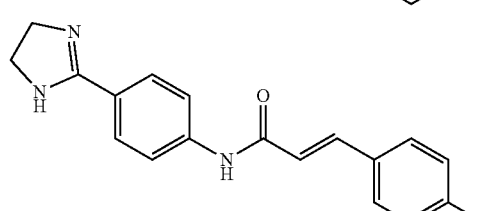
,

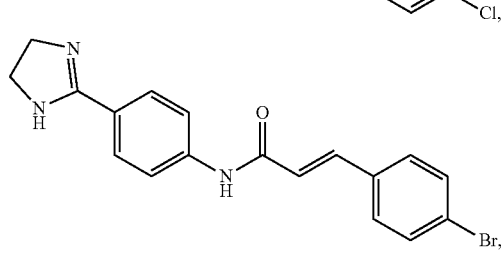
,

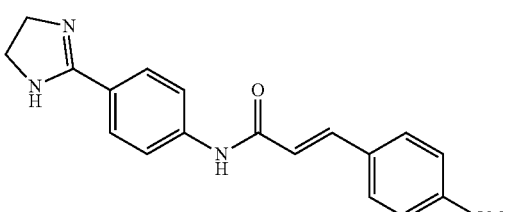
,

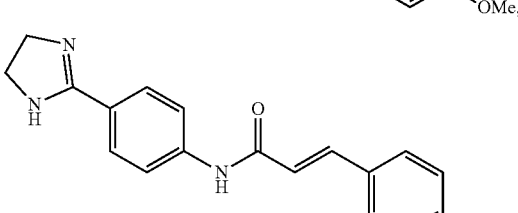
,

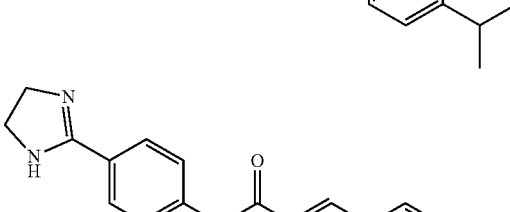
,

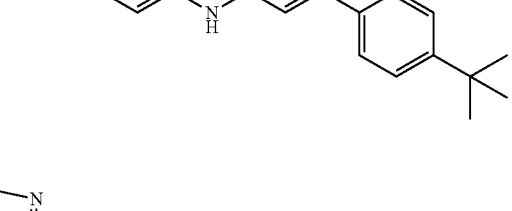
,

-continued
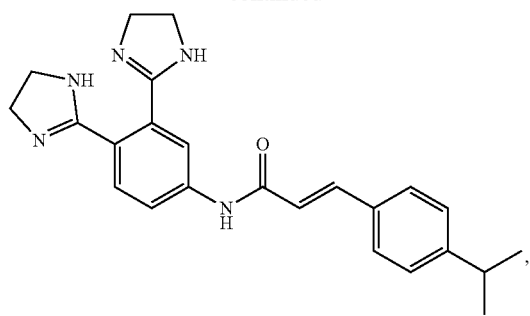
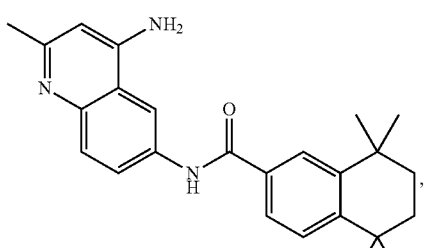
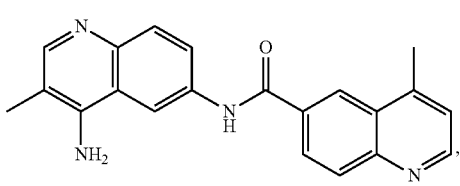
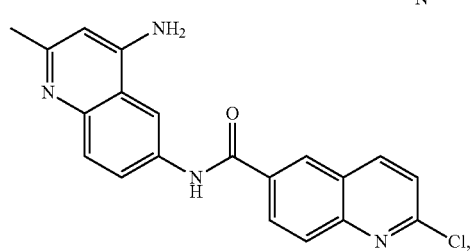
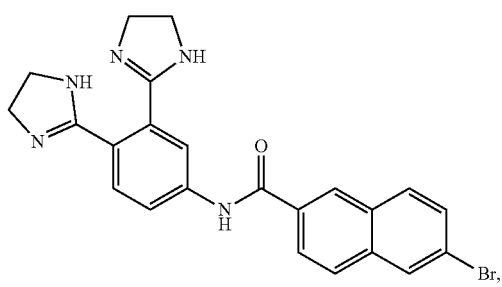
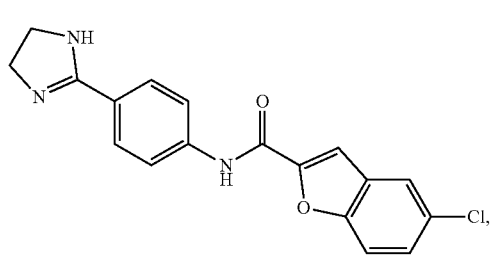
-continued
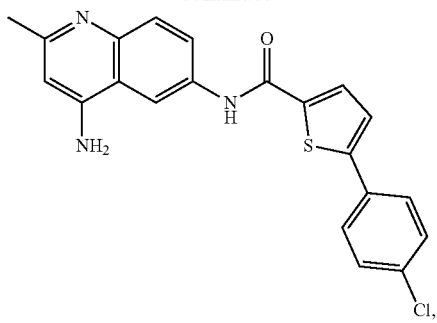
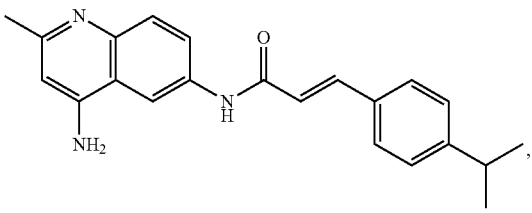
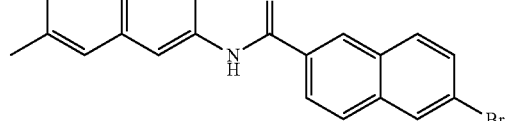
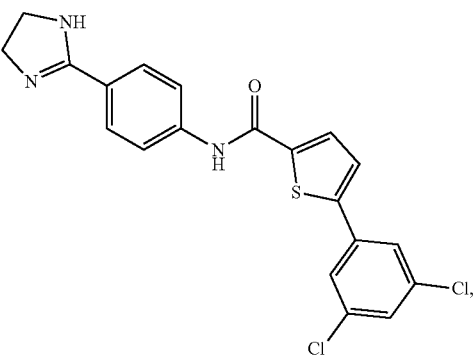
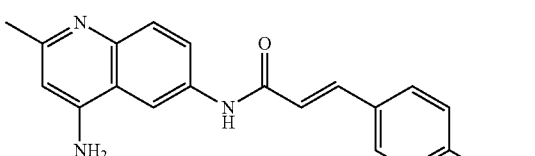
or a pharmaceutically acceptable salt thereof.
In still yet another aspect, the present disclosure provides method of measuring cellular growth or inhibition of a cellular membrane comprising:

(a) contacting a cell with a compound of the formula:

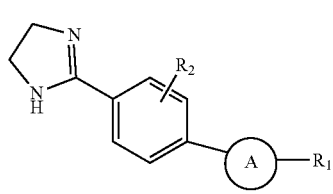

wherein:

A is arenediyl$_{(C\leq 12)}$, heteroarenediyl$_{(C\leq 12)}$, heterocycloalkanediyl$_{(C\leq 12)}$, or a substituted version of these groups, or —NR$_3$C(O)Y$_1$—; wherein:

R$_3$ is hydrogen, alkyl$_{(C\leq 6)}$, or substituted alkyl$_{(C\leq 6)}$;

Y$_1$ is a covalent bond, alkanediyl$_{(C\leq 12)}$, alkenediyl$_{(C\leq 12)}$, arenediyl$_{(C\leq 12)}$, heteroarenediyl$_{(C\leq 12)}$, or a substituted version of any of these groups;

R$_1$ is aryl$_{(C\leq 18)}$, substituted aryl$_{(C\leq 18)}$, heteroaryl$_{(C\leq 18)}$, or substituted heteroaryl$_{(C\leq 18)}$; and R$_2$ is hydrogen, amino, cyano, halo, hydroxy, or alkyl$_{(C\leq 8)}$, aryl$_{(C\leq 8)}$, aralkyl$_{(C\leq 8)}$, acyl$_{(C\leq 8)}$, alkoxy$_{(C\leq 8)}$, heteroaryl$_{(C\leq 12)}$, heterocycloalkyl$_{(C\leq 12)}$, alkylamino$_{(C\leq 8)}$, dialkylamino$_{(C\leq 8)}$, or a substituted version of any of these groups; or a compound of the formula:

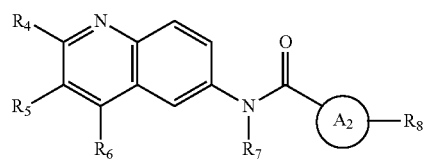

wherein:

A$_2$ is covalent bond, alkenediyl$_{(C\leq 12)}$, or substituted alkenediyl$_{(C\leq 12)}$;

R$_4$ and R$_5$ are each independently hydrogen, alkyl$_{(C\leq 8)}$, or substituted alkyl$_{(C\leq 8)}$;

R$_6$ is hydrogen, hydroxy, or amino; or alkoxy$_{(C\leq 8)}$, acyloxy$_{(C\leq 8)}$, alkylamino$_{(C\leq 8)}$, dialkylamino$_{(C\leq 8)}$, or a substituted version of any of these groups;

R$_7$ is hydrogen, alkyl$_{(C\leq 6)}$, or substituted alkyl$_{(C\leq 6)}$; and

R$_8$ is aryl$_{(C\leq 18)}$, substituted aryl$_{(C\leq 18)}$, heteroaryl$_{(C\leq 18)}$, substituted heteroaryl$_{(C\leq 18)}$;

or a pharmaceutically acceptable salt thereof.

(b) incubating said cell for sufficient time to permit uptake of said compound by said cell;

(c) measuring a fluorescent signal in said cell; and (d) measuring a change fluorescent signal in said cell as compared to step (c), wherein the change in fluorescent signal is a measure of cellular growth or inhibition.

In some embodiments, said compound is further defined as:

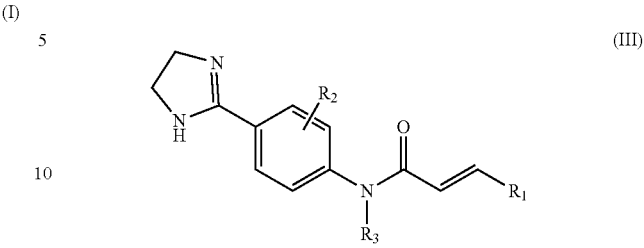

wherein:

R$_1$ is aryl$_{(C\leq 18)}$, substituted aryl$_{(C\leq 18)}$, heteroaryl$_{(C\leq 18)}$, or substituted heteroaryl$_{(C\leq 18)}$;

R$_2$ is hydrogen, amino, cyano, halo, hydroxy, and

R$_3$ is hydrogen, alkyl$_{(C\leq 6)}$, or substituted alkyl$_{(C\leq 6)}$;

or a pharmaceutically acceptable salt thereof.

In some embodiments, R$_2$ is hydrogen. In some embodiments, R$_3$ is hydrogen. In some embodiments, the methods further comprise quantitating the change in fluorescent signal. In some embodiments, the fluorescent signal is quantitated by fluorescence microscopy. In other embodiments, the fluorescent signal is quantitated by fluorometer.

In some embodiments, said cell is a bacterial cell. In some embodiments, said cell is a Gram-negative bacterial cell such as *Escherichia coli, Pseudomonas aeruginosa, Acinetobacter baumannii, Klebsiella* species, *Burkholderia* species, *Enterobacter* species or *Stenotrophomonas maltophilia*. In some embodiments, said bacterial cell is multidrug resistant. In other embodiments, said cell is a fungal cell such as a *Candida* species, *Saccharomyces* species, or *Aspergillus* species. In some embodiments, said cell is a cancer cell. In some embodiments, step (d) is performed at multiple time points following step (b).

It is contemplated that any embodiment discussed in this specification can be implemented with respect to any method or composition of the disclosure, and vice versa. Furthermore, compositions of the disclosure can be used to achieve methods of the disclosure.

The use of the word "a" or "an" in the claims and/or the specification may mean "one," but it is also consistent with the meaning of "one or more," "at least one," and "one or more than one."

The phrase "one or more" as found in the claims and/or the specification is defined as 1, 2, 3, 4, 5, 6, 7, 8, 9, 10, or more.

Throughout this application, the terms "about" and "approximately" indicate that a value includes the inherent variation of error for the device, the method being employed to determine the value, or the variation that exists among the study subjects. In one non-limiting embodiment the terms are defined to be within 10%, preferably within 5%, more preferably within 1%, and most preferably within 0.5%.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The disclosure may be better understood by reference to one or more of these drawings in combination with the detailed description of specific embodiments presented herein.

(FIG. 2A) A recombinant pore with an internal diameter of ~2.4 nm (Mohammad et al., 2011). (FIG. 2B) The pore is expressed in WT and Δ3 (ΔmexAB, ΔmexCD, ΔmexXY) strains and enables hypersusceptibility to vancomycin. Zones of inhibition with 10 μM discs of vancomycin and in the presence and absence of the inducer of pore expression are shown. (FIG. 2C)

DETAILED DESCRIPTION

Figure 1:
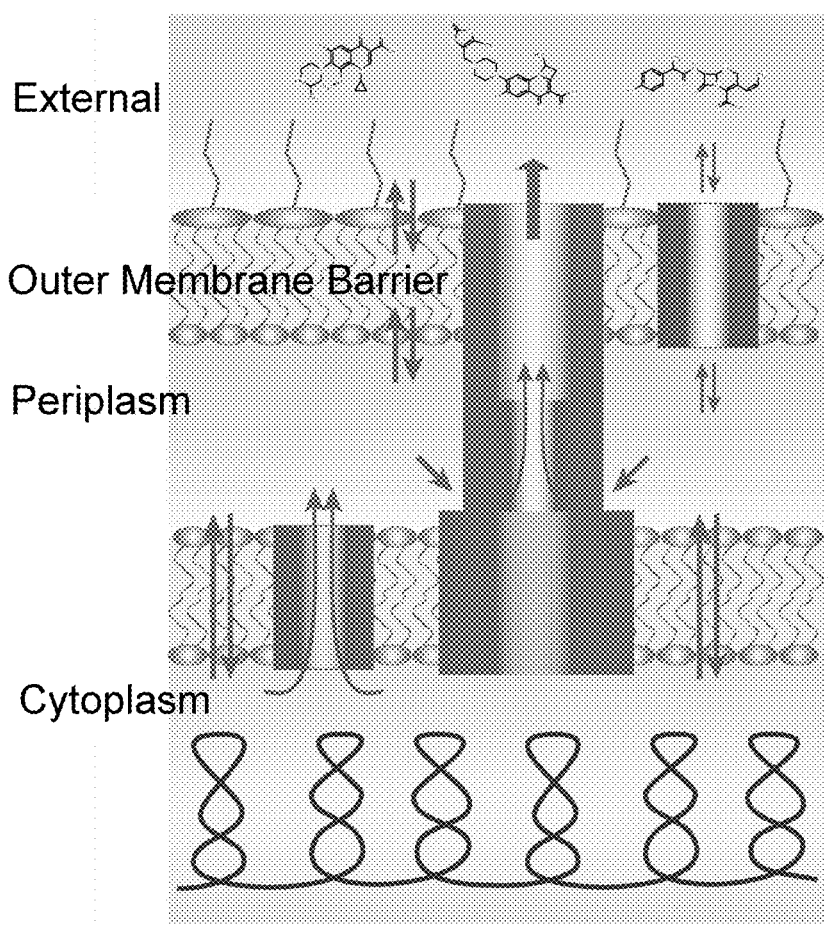
FIG. 1. Fluxes of antibiotics across Gram-negative cell envelope (Cyan arrows). Model of the major efflux pump of *P. aeruginosa* comprising the MFP MexA (Orange), the RND transporters MexB (Blue) and OprM (Red) is shown. The asymmetric OM bilayer is stabilized by $Mg^{2+}$ (magenta) and contains ~200,000 copies of a general porin OprF (yellow). Efflux across both IM and OM is present.

Multidrug resistant bacteria spread rapidly in hospitals and clinics. The major concerns relate to Gram negative bacteria (GNB) that, in addition to class-specific resistance, overproduce efflux pumps enabling resistance to a broad range of anti-microbial agents. GNB vary significantly in the diversity and properties of efflux pumps and new tools are needed to characterize the strains that overproduce efflux pumps and establish their specificity.

The inventors here describe a series of compounds with the same structural core that are essentially non-fluorescent in water but produce significant fluorescence once inside bacterial cells. They also lack potent antibacterial activity, thereby avoiding confounding results based on such activities. The intensity and rates of fluorescence changes in bacterial strains contacted with these compounds can permit assessment of bacterial cell membrane permeability as well as efflux pump activity, including specificity. These and other aspects of the disclosure are discussed in detail below.

I. EFFLUX AND MULTIDRUG RESISTANCE

A. Efflux Pumps

Efflux pumps are transporters localized in the cytoplasmic membrane of all kinds of cells, including bacteria. They are active transporters, meaning that they require a source of chemical energy to perform their function. Some are primary active transporters utilizing adenosine triphosphate hydrolysis as a source of energy, whereas others are secondary active transporters (antiporters) in which transport is coupled to an electrochemical potential difference created by pumping hydrogen or sodium ions from or to the outside of the cell.

Bacterial efflux transporters are classified into five major superfamilies, based on their amino acid sequence and the energy source used to export their substrates:

the major facilitator superfamily (MFS)
the ATP-binding cassette superfamily (ABC)
the small multidrug resistance family (SMR)
the resistance-nodulation-cell division superfamily (RND)
the Multi antimicrobial extrusion protein family (MATE).

Of these, only the ABC superfamily are primary transporters, the rest being secondary transporters utilizing proton or sodium gradient as a source of energy. Whereas MFS dominates in Gram positive bacteria, the RND family was once thought to be unique to GNB. They have since been found in all major Kingdoms.

Although antibiotics are the most clinically important substrates of efflux systems, it is probable that most efflux pumps have other natural physiological functions. Examples include the *E. coli* AcrAB efflux system, which has a physiologic role of pumping out bile acids and fatty acids to lower their toxicity. The MFS family Ptr pump in *Streptomyces pristinaespiralis* appears to be an autoimmunity pump for this organism when it turns on production of pristinamycins I and II. The AcrAB-TolC system in *E. coli* is suspected to have a role in the transport of the calcium-channel components in the *E. coli* membrane. The MtrCDE system plays a protective role by providing resistance to fecal lipids in rectal isolates of *Neisseria gonorrhoeae*. The AcrAB efflux system of *Erwinia amylovora* is important for this organism's virulence, plant (host) colonization, and resistance to plant toxins. The MexXY component of the MexXY-OprM multidrug efflux system of *P. aeruginosa* is inducible by antibiotics that target ribosomes via the PA5471 gene product.

The ability of efflux systems to recognize a large number of compounds other than their natural substrates is probably because substrate recognition is based on physicochemical properties, such as hydrophobicity, aromaticity and ionizable character rather than on defined chemical properties, as in classical enzyme-substrate or ligand-receptor recognition. Because most antibiotics are amphiphilic molecules—possessing both hydrophilic and hydrophobic characters—they are easily recognized by many efflux pumps.

The impact of efflux mechanisms on antimicrobial resistance is large; this is usually attributed to the following. The genetic elements encoding efflux pumps may be encoded on chromosomes and/or plasmids, thus contributing to both intrinsic (natural) and acquired resistance respectively. As an intrinsic mechanism of resistance, efflux pump genes are important for survival in a hostile environment (for example in the presence of antibiotics) which allows for the selection of mutants that over-express these genes. Being located on transportable genetic elements as plasmids or transposons is also advantageous for the microorganisms as it allows for the easy spread of efflux genes between distant species.

Expression of several efflux pumps in a given bacterial species may lead to a broad spectrum of resistance when considering the shared substrates of some multi-drug efflux pumps, where one efflux pump may confer resistance to a wide range of antimicrobials. Common multidrug-resistant organisms are Vancomycin-Resistant Enterococci (VRE), Methicillin-Resistant *Staphylococcus aureus* (MRSA), Extended-spectrum β-lactamase (ESBLs) producing GNB, *Klebsiella pneumoniae* carbapenemase (KPC) producing GNB, and Multi-Drug-Resistant GNB (MDR GNR), such as *Enterobacter* species, *E. coli, Klebsiella pneumoniae, Acinetobacter baumannii, Pseudomonas aeruginosa*. A group of Gram-positive and Gram-negative bacteria of particular recent importance have been dubbed as the ESKAPE group (*Enterococcus faecium, Staphylococcus aureus, Klebsiella pneumoniae, Acinetobacter baumannii, Pseudomonas aeruginosa* and *Enterobacter* species).

B. Multidrug Resistance

The development and spread of antibiotic resistance in bacteria is a universal threat to both humans and animals (Bush et al., 2011). The economic and human cost of antibiotic resistance is tremendous. Some pathogens have acquired resistance to multiple antibiotics and cause infections that are effectively untreatable. Among pathogenic GNB *Acinetobacter, Pseudomonas* and *Enterobacteriaceae*, a number of species have emerged that are resistant to all antibiotics (Livermore, 2004). Thus, there is a strong need for new antibiotics, particularly those directed against MDR GNB (WHO-PPL-Short_Summary_25Feb). However, antibiotic discovery and development against these pathogens are hampered by the elaborate organization of their cell envelopes, which effectively exclude numerous chemicals from the cell interior (Silver, 2011).

On biological level, the mechanisms that limit drug accumulation are well understood (Silver, 2011; Silver, 2016; Awoonor-Williams et al., 2016; Nikaido & Pages, 2012 and Zgurskaya et al., 2015). Drug penetration into GNB is governed by two opposing fluxes across the two membranes of these species (Silver, 2011; Zgurskaya et al., 2009 and Lewis, 2012). The influx and uptake of antibiotics are significantly slowed down by the elaborate outer membrane (OM) (FIG. 1). This membrane is an asymmetric bilayer of lipopolysaccharides (LPS) and phospholipids, into which non-specific porins and highly specific uptake channels are embedded (Nikaido, 2003). The LPS-containing bilayer reduces diffusion of hydrophobic compounds, whereas narrow pores limit by size the penetration of hydrophilic drugs (Zgurskaya et al., 2015).

The slow influx of drugs across the OM is further opposed by active export mediated by multidrug efflux transporters. Several families of transporters capable of multidrug efflux have been identified (Lomovskaya et al., 2008; Zgurskaya, 2009 and Ruggerone et al., 2013). The most effective transporters belong to the RND superfamily and confer resistance to clinically significant antibiotics by associating with the periplasmic and OM accessory proteins to form trans-envelope complexes (Lomovskaya, et al., 2007) (FIG. 1). Ultimately, these efflux machines enable conversion of the energy stored in the inner membrane into active transport of antibiotics across the OM (OM efflux). Importantly, mutational inactivation or inhibition of efflux pumps dramatically potentiate activities of various antibiotics in GNB, pointing out the central role of active efflux in limiting drug permeation into GNB (Lomovskaya et al., 1999; Lomovskaya et al., 2001; Sjuts et al., 2016; Vargiu et al., 2014; Li et al., 2003 and Li et al., 2000). Furthermore, in the absence of efflux, target mutations fail to produce clinical levels of antibiotic resistance, further vouching for the effectiveness of efflux avoidance and inhibition in sensitization of multidrug resistant clinical isolates to antibiotics (Lomovskaya et al., 1999; Oethinger et al., 2000; Fange et al., 2009 and Lovmar et al., 2009).

II. COMPOUNDS OF THE PRESENT DISCLOSURE

The compounds of the present disclosure are shown, for example, above, in the summary section, in the claims below, and Table 1 in the Examples.

The compounds may be made using the synthetic methods outlined in the Examples section. These methods can be further modified and optimized using the principles and techniques of organic chemistry as applied by a person skilled in the art. Such principles and techniques are taught, for example, in Smith, *March's Advanced Organic Chemistry: Reactions, Mechanisms, and Structure*, (2013), which is incorporated by reference herein. In addition, the synthetic methods may be further modified and optimized for preparative, pilot- or large-scale production, either batch or continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

In some embodiments, the compounds of the present disclosure have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, improved cell penetration/accumulation and/or have other useful pharmacological, physical, or chemical properties over, compounds known in the prior art, whether for use in the indications stated herein or otherwise.

Compounds of the present disclosure may contain one or more asymmetrically-substituted carbon or nitrogen atoms and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent compounds of the present disclosure will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the compounds of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will be appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present disclosure.

A. Chemical Group Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means=NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means=S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, the formula

covers, for example,

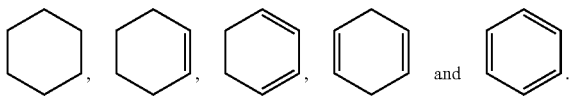

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol " ∿ ", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "⋯" means a single bond where the group attached to the thick end of the wedge is "into the page". The symbol " ∿ " means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

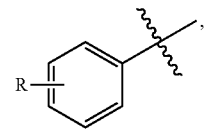

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

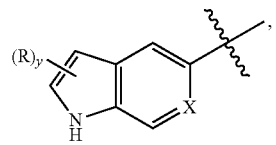

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-}$ 10)" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. When any of the chemical groups or compound classes defined herein is modified by the term "substituted", any carbon atom(s) in the moiety replacing a hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group refers to a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

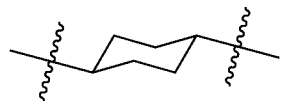 [SMILES: *C1CCC(*)CC1]

is a non-limiting example of cycloalkanediyl group. A "cycloalkane" refers to the class of compounds having the formula H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more aromatic ring structure, wherein the ring atoms are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl or cycloalkyl groups (carbon number limitation permitting) attached to the first aromatic ring or any additional aromatic ring present. If a cycloalkyl groups is present, such a group may be fused to one or more of the aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl (e.g., 4-phenylphenyl). The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

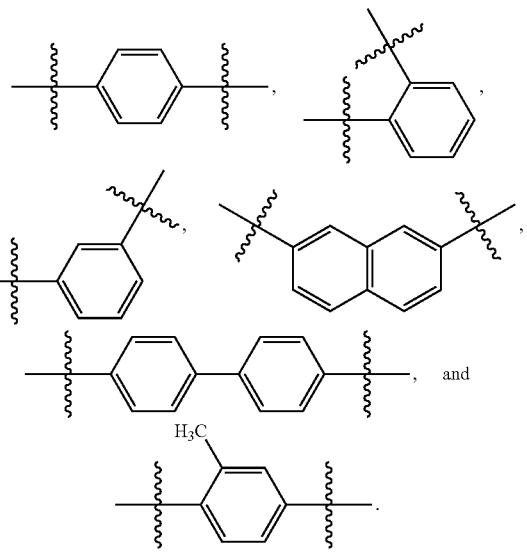

and

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, the aromatic ring structures being one, two, three, or four ring structures each containing from three to nine ring atoms, and wherein the heteroaryl group consists of no atoms other than carbon, hydrogen, aromatic nitrogen, aromatic oxygen and aromatic sulfur. If more than one ring is present, the rings may be fused or unfused. Unfused rings are connected with a covalent bond. As used herein, the term heteroaryl does not preclude the presence of one or more alkyl or aryl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings are connected with a covalent bond. As used herein, the term heteroarenediyl does not preclude the presence of one or more alkyl or aryl groups (carbon number limitation permitting) attached to the aromatic ring or aromatic ring system. Non-limiting examples of heteroarenediyl groups include:

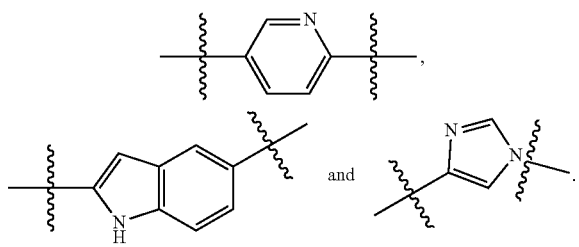

The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, the non-aromatic ring structures being one, two, three, or four ring structures each containing from three to nine ring atoms, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. The term "heterocycloalkanediyl" when used without the "substituted" modifier refers to an divalent cyclic group, with two carbon atoms, two nitrogen atoms, or one carbon atom and one nitrogen atom as the two points of attachment, said atoms forming part of one or more ring structure(s) wherein at least one of the ring atoms is nitrogen, oxygen or sulfur, and wherein the divalent group consists of no atoms other than carbon, hydrogen, nitrogen, oxygen and sulfur. If more than one ring is present, the rings may be fused or unfused. Unfused rings are connected with a covalent bond. As used herein, the term heterocycloalkanediyl does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkanediyl groups include:

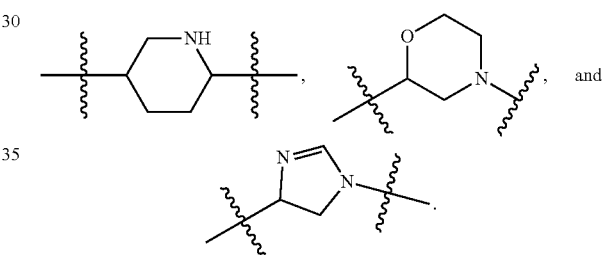

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH(CH$_2$)$_2$, —C(O)C$_6$H$_5$, and —C(O)C$_6$H$_4$CH$_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)

$CH_2CF_3$, —$CO_2H$ (carboxyl), —$CO_2CH_3$ (methylcarboxyl), —$CO_2CH_2CH_3$, —$C(O)NH_2$ (carbamoyl), and —$CON(CH_3)_2$, are non-limiting examples of substituted acyl groups.

The term "alkoxy" when used without the "substituted" modifier refers to the group —OR, in which R is an alkyl, as that term is defined above. Non-limiting examples include: —$OCH_3$ (methoxy), —$OCH_2CH_3$ (ethoxy), —$OCH_2CH_2CH_3$, —$OCH(CH_3)_2$ (isopropoxy), or —$OC(CH_3)_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$C(O)NHCH_3$, —$C(O)N(CH_3)_2$, —$OC(O)CH_3$, —$NHC(O)CH_3$, —$S(O)_2OH$, or —$S(O)_2NH_2$.

The term "alkylamino" when used without the "substituted" modifier refers to the group —NHR, in which R is an alkyl, as that term is defined above. Non-limiting examples include: —$NHCH_3$ and —$NHCH_2CH_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —$N(CH_3)_2$ and —$N(CH_3)(CH_2CH_3)$. The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —$NHC_6H_5$. The term "amido" (acylamino), when used without the "substituted" modifier, refers to the group —NHR, in which R is acyl, as that term is defined above. A non-limiting example of an amido group is —$NHC(O)CH_3$. The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$C(O)NHCH_3$, —$C(O)N(CH_3)_2$, —$OC(O)CH_3$, —$NHC(O)CH_3$, —$S(O)_2OH$, or —$S(O)_2NH_2$. The groups —$NHC(O)OCH_3$ and —$NHC(O)NHCH_3$ are non-limiting examples of substituted amido groups.

III. ASSAYS FOR USE IN MEASURING PERMEABILITY AND EFFLUX ACTIVITY

A. LC-MS

In one aspect, applicants will employ liquid chromatography-mass spectrometry (LC-MS) to analyze effects of the compounds described above on efflux activity. LC-MS is an analytical chemistry technique that combines the physical separation capabilities of liquid chromatography (or HPLC) with the mass analysis capabilities of mass spectrometry (MS). Coupled chromatography—MS systems are popular in chemical analysis because the individual capabilities of each technique are enhanced synergistically. While liquid chromatography separates mixtures with multiple components, mass spectrometry provides structural identity of the individual components with high molecular specificity and detection sensitivity. This tandem technique can be used to analyze biochemical, organic, and inorganic compounds commonly found in complex samples of environmental and biological origin. Therefore, LC-MS may be applied in a wide range of sectors including biotechnology, environment monitoring, food processing, and pharmaceutical, agrochemical, and cosmetic industries.

In addition to the liquid chromatography and mass spectrometry devices, an LC-MS system contains an interface that efficiently transfers the separated components from the LC column into the MS ion source. The interface is necessary because the LC and MS devices are fundamentally incompatible. While the mobile phase in a LC system is a pressurized liquid, the MS analyzers commonly operate under vacuum (around $10^{-6}$ torr). Thus, it is not possible to directly pump the eluate from the LC column into the MS source. Overall, the interface is a mechanically simple part of the LC-MS system that transfers the maximum amount of analyte, removes a significant portion of the mobile phase used in LC and preserves the chemical identity of the chromatography products (chemically inert). As a requirement, the interface should not interfere with the ionizing efficiency and vacuum conditions of the MS system. Nowadays, most extensively applied LC-MS interfaces are based on atmospheric pressure ionization (API) strategies like electrospray ionization (ESI), atmospheric pressure chemical ionization (APCI), and atmospheric pressure photoionization (APPI). These interfaces became available in the 1990s after a two decade long research and development process.

B. Fluorescence-Based Efflux Inhibition Assay

In another aspect, applicants will employ fluorescence of free Hoechst or compounds and their DNA- and lipid-bound forms to analyze the effect of inhibitors on efflux as described before in Westfall et al (Westfall et al., 2009). For calibration, Hoechst and compound solutions will be mixed with different amounts of salmon sperm DNA (Invitrogen Inc.) in buffer containing 50 mM HEPES-KOH (pH 7.0), 1 mM MgSO4 and 0.4% glucose (HMG buffer). Both direct and serial dilutions will be prepared in a black F-bottom non-binding 96-well plate (Greiner Bio-One, Inc.). $OD_{600}$ 1.0 of E. coli cells is assumed to contain 17 µg of DNA. In parallel, the corresponding solutions of free Hoechst and compounds in HMG buffer will be prepared. The plates containing DNA-bound and free Hoechst will be incubated for different periods of time up to 120 min and emission spectra will be collected in a Tecan Spark 10M plate reader at $\lambda_{ex}$=355 nm and $\lambda_{em}$ from 400 nm to 550 nm with a Z-value setting of 25000 and a gain of 75. At these conditions, fluorescence of free Hoechst was found to have emission maximum at $\lambda_{em}$=500 nm and its DNA-bound form at $\lambda_{em}$=450 nm and the intensity remained the same for up to 120 min. The signal-response curve for the reader was found linear over the entire range of measurements.

Similar calibrations will be carried out with purified *E. coli* lipids (a polar fraction, Avanti Lipids Inc.) and lysed ΔTolC-Pore cells. Dry lipids were reconstituted in HMG buffer and briefly sonicated in a water bath sonicator (Branson Inc.). The lipid suspension containing 27 μg, 13.5 μg and 2.7 μg of lipids, which correspond to lipid contents of *E. coli* cells at $OD_{600}$ of 1.0, 0.5, 0.1 will be mixed with Hoechst and other compound solutions as described for DNA calibrations. Cell lysates will be prepared by sonication and freeze-thawing of exponentially grown *E. coli* cells collected by centrifugation and resuspended in HMG buffer to $OD_{600}$ 2.0. Lysates will be mixed with Hoechst solutions to obtain final amounts of lysed cells corresponding to $OD_{600}$ of 1.0, 0.5, 0.25 and 0.1.

For Hoechst or compound uptake experiments, overnight grown cells will be re-inoculated into 30 ml LB broth and grown until $OD_{600}$ of 1. The cells will then pelleted by centrifugation for 15 min at room temperature and washed once in HMG buffer. The pellet will be resuspended in HMG buffer to $OD_{600}$ of 2.0 and kept at room temperature during the course of the experiment. For the efflux inhibition or uptake kinetics, 100 μl of Hoechst or compound solution in HMG buffer with and without increasing concentrations of inhibitors at twice the concentrations indicated will be added into a black F-bottom non-binding 96-well plate. Fluorescence of Hoechst or compounds will be followed at $\lambda_{ex}$=355 nm and $\lambda_{em}$=450 nm. To this, 100 μl of cells at $OD_{600}$ of 2.0 was injected, shaken for 6 sec and the fluorescence of Hoechst will be monitored continuously for up to 10 min.

C. Investigational Antibacterial Agents

The inventors screened NCI Diversity sets in *E. coli* BW25113 and *P. aeruginosa* PAO1 for antibacterial and EPI activities. From ~2,000 compounds tested, the inventors identified 34 active compounds (Abdali et al., 2017). One of these actives was further profiled in detail to determine their mechanisms of actions and penetration properties: A phthalanilide compound NSC 60339 (CA798859A), which was found to have both antibacterial and anti-MFP (Membrane Fusion Protein, FIG. 1) activities and was a modest substrate of efflux pumps (Abdali et al., 2017). Preliminary work on NSC 60339 has produced 75 analogs with comparable anti-target activities but reduced efflux Abdali et al., 2017). Synthetic procedures for modifying NSC 60339 has been described before (Abdali et al., 2017 and Gamage et al., 2013). Because clinically-important antibiotics are extensively optimized, the inventors have chosen to focus on fluoroquinolones, tetracyclines, oxazolidinones, phenicols and macrolides/ketolides representatives that are known to penetrate through both the LPS-phospholipid bilayer and porins of the OM and include both broad and narrow spectrum antibiotics.

For assessing antibacterial activities, compounds will be analyzed against four strains of *P. aeruginosa*: WT and ΔEfflux (lacking mexAB-OprM, mexCD-OprJ, mexXY), and their hyperporinated variants WT-Pore and ΔEfflux-Pore (FIGS. 2A-C) (Krishnamoorthy et al., 2016 and Krishnamoorthy et al., 2017). Based on minimal inhibitory concentrations (MIC) and growth $IC_{50}$, compounds will be grouped as affected by efflux or by OM barriers. Compounds affected by MexB efflux will be defined as the compounds whose MIC ratios WT/ΔEfflux and WT-Pore/ΔEfflux-Pore are greater than 4. Compounds affected largely by the OM barrier will be defined as compounds with the MIC ratios WT/WT-Pore and ΔEfflux/ΔEfflux-Pore greater than 4. The inventors expect that at least 50% of the compounds in the library will have antibacterial activities in the hyperporinated efflux-deficient ΔEfflux-Pore. The -fold changes in MICs in the four strains will be used to guide selection of the compounds for detailed studies.

D. Permeability Properties of Compounds of the Present Disclosure

Figure 2:
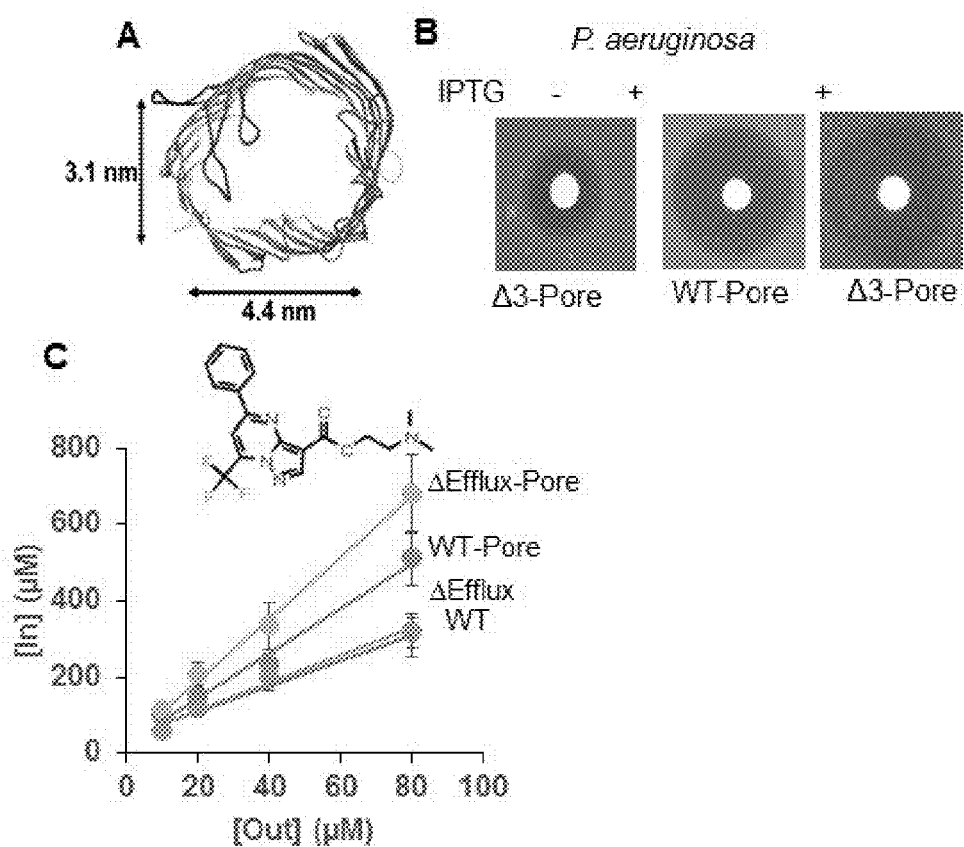
FIGS. 2A-C. Hyperporination and LC/MS analyses of compound uptake into four strains of *P. aeruginosa*.

The inventors developed an experimental approach to control the permeability properties of the OM in live cells without changing the structure of membranes (Krishnamoorthy et al., 2016) (FIGS. 2A-B). The hyperporination of the OM separates contributions of the OM barrier and active efflux to activities of antibiotics and for the first time allows separate analyses of SARs for efflux and the OM barrier, especially when combined with kinetic analysis (Westfall et al., 2009). The inventors will apply this methodology to establish relationships between properties of EPIs and antibacterial agents and active efflux and OM permeability in *P. aeruginosa* cells. All compounds will be analyzed for penetration into six strains of *P. aeruginosa*, and the inhibitory activities of EPIs in this set will be measured through their effect on accumulation of fluorescent reporters.

To measure intracellular uptake of compounds, the inventors will use a direct assay in which changes in the intracellular concentration of a compound with concentration and time are measured using LC/MS (Davis et al., 2014; Cai et al., 2009 and Richter et al., 2017). In preliminary studies, they have validated the LC/MS assay, which is sensitive (limit of detection <1 ng/ml), reproducible and is optimized for a 96-well microplate format (FIG. 2C).

For the uptake experiments, the inventors will use the four strains of *P. aeruginosa*. Cells will be transferred into a defined medium containing increasing concentrations of compounds. They will first measure steady-state accumulation at six concentrations (8 μM to 128 μM) and two timepoints (1 min, 40 min). Cells will be filtered, dried and extracted by sonication with ice cold methanol and 1:1 methanol:water. The extracts will be analyzed on Agilent 6545 QTOF instrument (see Letters). Intracellular concentration will be plotted as a function of external concentration and time. The difference in slopes in efflux-plus and -minus strains will be a measure of the efflux efficiency, while the difference in slopes between ΔEfllux and ΔEfflux-Pore strains will inform on the OM barrier (FIG. 2C). Identical slopes at the two timepoints will be interpreted as fast accumulation kinetics, with steady state reached within 1 min. In contrast, significantly different slopes would indicate slow accumulation, and for these compounds, the inventors will reanalyze at eight timepoints to determine accumulation rates. The data will be analyzed to derive a full set of kinetic parameters.

Figure 3:
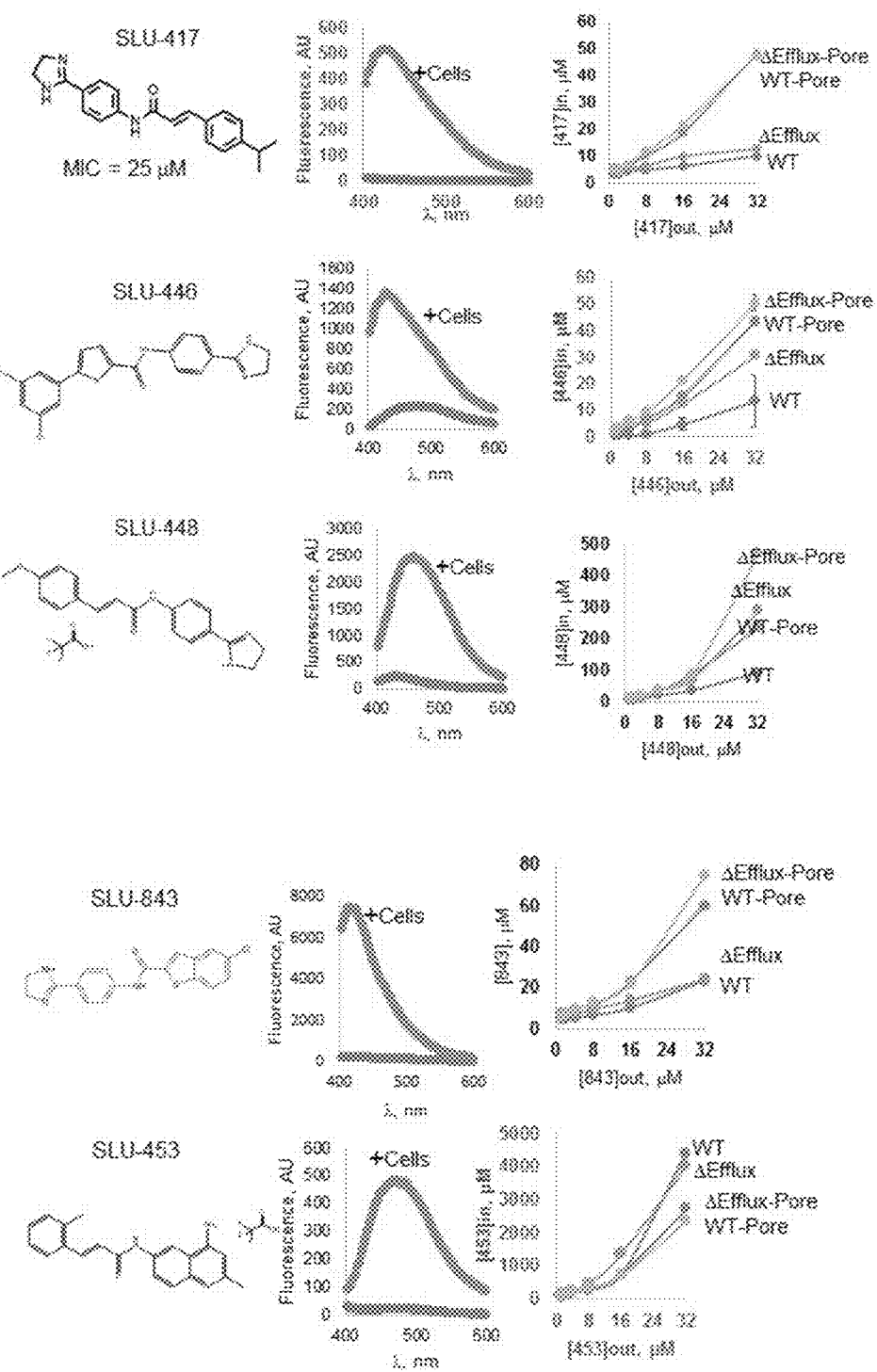
FIG. 3. Structure (left), cell-dependent fluorescence emission spectra at excitation 335 nm (middle) and intracellular uptake (right) of SLU-417, SLU-446, SLU-448, SLU-843, SLU-453. Note that uptake of SLU-417, -446, -448 and -843 increases when the cell envelope is compromised.

The inventors will use a fluorescence-based assay in which a fluorescent probe, a substrate of efflux pumps, reports EPI activities. Exponentially grown cells will be transferred into a defined medium, dispensed into 96-well plates with increasing concentrations of EPIs, and incubated for a pre-determined time. The probe will be added to cells and fluorescence recorded at different time points. Compounds with efflux inhibiting activities will increase the uptake of the probe and as a result increase the probe fluorescence (FIG. 3) (Abdali et al., 2017). The reverse kinetic curves, in which the concentration of the compound is fixed while the probe concentration varies, will be also collected. Detailed quantification of the kinetic data will be performed using two probes: a DNA dye Hoechst 33342 (HT) (Eicher et al., 2012; Nakashima et al., 2011 and Richmond et al., 2013) and a novel SLU-417 probe that were synthesized during a focused synthetic effort (Haynes et al., 2017). HT is a topoisomerase inhibitor with the MIC 2 μM in Δ6-Pore cells. In contrast, SLU-417 is relatively inert with MIC≥50 μM, which should reduce possible non-specific effect during drug uptake measurements. Preliminary data showed that both these probes perform well in 96-well format and that at least a three-fold difference in the fluorescence intensity of the probe is achievable in the efflux-proficient and -deficient cells (FIG. 3).

IV. KITS

Any of the compositions described herein may be comprised in a kit. In a non-limiting example, a compound according to the present disclosure is included in a kit. The kit may further include materials to run control reactions. The kit may also contain materials for the culture of bacteria, including appropriate media and supplements. The kit may further comprise instruction for performing reactions, including control reaction and measurements.

In still further embodiments, the kits may provide suitable container means, such as a solid support, such as a column matrix and/or well of a microtiter plate. The container means of the kits may also include at least one vial, test tube, flask, bottle, syringe, tray, plate or other container means, into which a component may be placed, and preferably, suitably aliquoted. Where there is more than one component in the kit, the kit also will generally contain a second, third or other additional container into which the additional components may be separately placed. However, various combinations of components may be comprised in a vial.

The kits of the present disclosure also will typically include a means close confinement of containers for commercial sale. Such containers may include injection or blow-molded plastic containers into which the desired vials are retained. Instructions may include variations that can be implemented.

When the components of the kit are provided in one and/or more liquid solutions, the liquid solution is an aqueous solution, with a sterile aqueous solution being particularly preferred. However, the active agent may be provided as dried powder(s). When reagents and/or components are provided as a dry powder, the powder can be reconstituted by the addition of a suitable solvent. It is envisioned that the solvent may also be provided in another container means. Such kits may also include components that preserve or maintain the active agent that protect against its degradation.

V. EXAMPLES

The following examples are included to demonstrate certain non-limiting aspects of the disclosure. It should be appreciated by those of skill in the art that the techniques disclosed in the examples which follow represent techniques discovered by the inventor to function well in the practice of the disclosure. However, those of skill in the art should, in light of the present disclosure, appreciate that many changes can be made in the specific embodiments which are disclosed and still obtain a like or similar result without departing from the spirit and scope of the disclosure.

Example 1

Experiments were carried out in four *E. coli* strains, BW25113, a wild type strain with efflux pumps, ΔEfflux, a cell line in which the efflux pumps have been inactivated by removal of tolC gene and their hyperporinated variants WT-Pore and ΔEfflux-Pore. Four compounds were tested in these cell lines which show increased fluorescence intensity in cells in which the efflux pumps have been removed (FIG. 3). Finally, the emission spectra was collected for each of these compounds which show that in the presence of cells, the compounds fluorescence while without cells, the compounds show little to no background fluorescence. See FIG. 3.

Example 2

General Synthetic Procedures.

Compounds of the present invention can be categorized into two basic structural classes, dihydroimidazolines (I) and diaminoquinolines (II) and were prepared as summarized below. Compounds belonging to type (I) were synthesized from 4-(4,5-dihydro-1H-imidazol-2-yl)aniline (3). Aniline 3 was prepared from 4-aminobenzonitrile using the outlined literature procedure (Sun et al, 2008). The bis-substituted imidazoline 5 was prepared in an analogous manner. Coupling of either 3 or 5 with the requisite acid chlorides in acetic acid (Hagmann, 1998) following the known procedure gave rise to dihydroimidazolines of type (I).

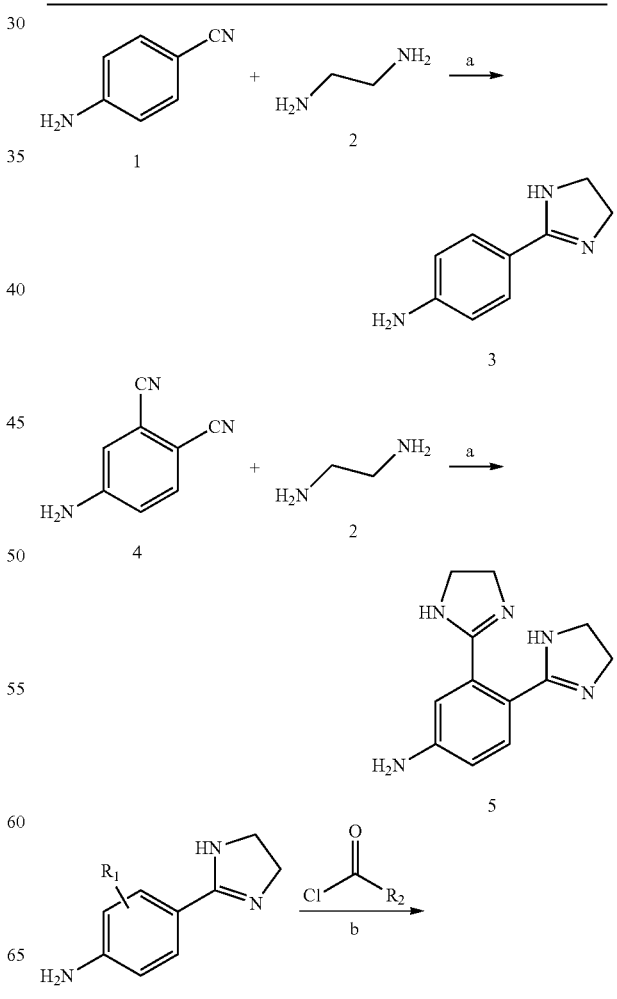

Scheme 1. Synthetic procedures for the preparation of dihydroimdazoline compounds.

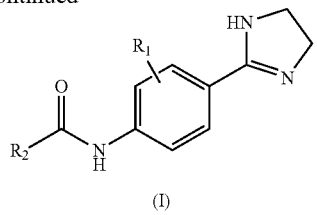

Conditions: (a) NaSH, Dimethylacetamide, 100° C., 10-15 h. (b) HOAc(gl), rt, overnight The quinolone structures of type (II) were prepared from coupling of 3-methylquinoline-4,7-diamine (8) with various acid chlorides in acetic acid. Quinoline 8 was prepared in two steps from acetone and 2-amino-5-nitrobenzonitrile (6). Condensation of 6 with acetone gave rise to the nitroquinolone 7. Reduction of the nitro group with nickel/aluminum alloy at 60° C. gives rise to the diamine 8. Reaction of 8 with various acid chlorides using glacial acetic acid gives rise selectively to the desired substituted quinolones of type (II).

Scheme 2. Synthesis of diaminoquinoline compounds.

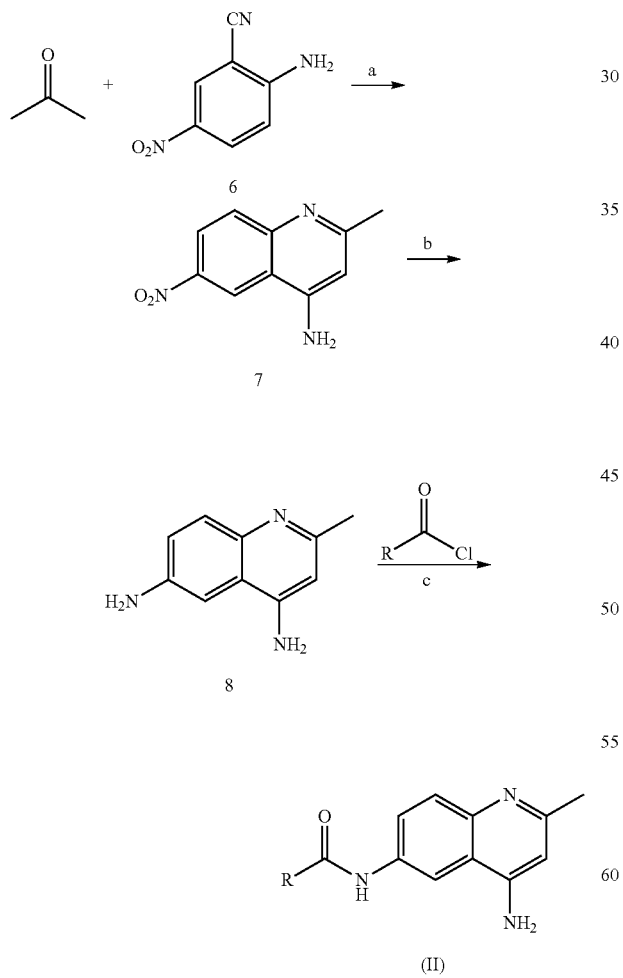

Conditions: (a) Tin(iv)chloride, toluene, reflux, 12 h, (b), Nickel/aluminum alloy, 60° C., 2 h (c) HOAc (gl), rt, 4 h

Example 3

Experimental Details

Synthesis of 3,4-bis(4,5-dihydro-1H-imidazol-2-yl) aniline 3-TFA (5)

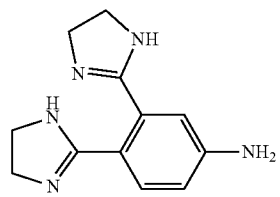 [SMILES: Nc1ccc(C2=NCCN2)c(C2=NCCN2)c1]

4-aminophthalonitrile (358 mg, 2.5 mmol) was added to a reaction vial along with sodium hydrosulfide hydrate (608 mg, 10 mmol). Dimethylacetamide (1.0 mL) was added before ethylenediamine (3.34 mL, 50 mmol) and the reaction was heated at 110° C. for 12 hours. Solvent was removed and crude product was purified on a 50 g C18 reversed-phase column (acetonitrile/water w/0.05% TFA). Product was isolated as a 3-TFA salt (712 mg, 50% yield).

Synthesis of N-(4-(4,5-dihydro-1H-imidazol-2-yl) phenyl)cinnamamide

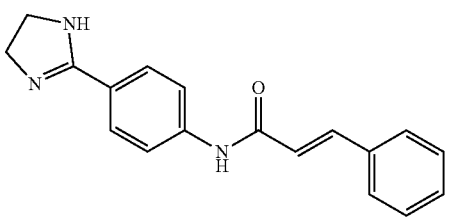 [SMILES: O=C(/C=C/c1ccccc1)Nc1ccc(C2=NCCN2)cc1]

4-(4,5-dihydro-1H-imidazol-2-yl)aniline (0.3 mmol) was dissolved in 1.5 mL glacial acetic acid and stirred at rt for 5 min. To this mixture was added cinnamoyl chloride (0.36 mmol). The resulting mix was sonicated to mix before being allowed to react overnight at room temperature. The solvent was removed and crude product was purified on a 50 g C18 reversed-phase column (acetonitrile/water). The product was obtained as the TFA salt. A tan solid, yield: 20%; $^1$H NMR (400 MHz, DMSO-$d_6$) δ 13.48 (s, 1H) 10.90 (s, 1H), 8.81 (d, J=2.4 Hz, 1H), 8.71 (s, broad, 2H), 8.67 (s, 1H), 8.36 (d, J=2.0 Hz, 1H), 8.09 (m, 4H), 7.86 (d, J=8.8 Hz, 1H), 7.78 (dd, J=8.8, 2.0 Hz, 1H), 6.61 (s, 1H), 2.60 (s, 3H); $^{13}$C NMR (400 MHz, DMSO-$d_6$) δ 164.41, 164.31, 144.82, 141.54, 134.46, 130.18, 129.73, 129.11, 127.96, 121.56, 118.96, 116.19, 44.29; HRMS: m/z calcd. for $C_{18}H_{17}N_3O$ [M+H]$^+$: 292.1452; found [M+H]$^+$: 292.1449.

Synthesis of (E)-N-(4-amino-2-methylquinolin-6-yl)-3-(3-chlorophenyl)acrylamide (384)

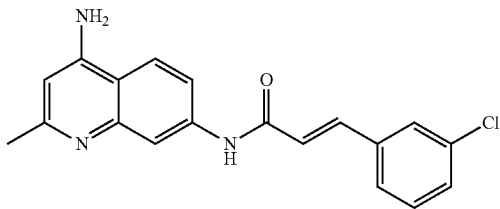 [SMILES: Cc1cc(N)c2ccc(NC(=O)/C=C/c3cccc(Cl)c3)cc2n1]

3-chlorocinnamic acid (0.25 mmol) was converted to the corresponding acid chloride via treatment with 2.0 M oxalyl chloride solution (0.3 mmol) in dichloromethane. A catalytic quantity of dimethylformamide was added and the reaction was judged complete in 4 hours on an ice bath. The solvent was removed leaving 3-chlorocinnamoyl chloride as a yellow solid. 2-methylquinoline-4,6-diamine (0.25 mmol) was dissolved in 1.5 mL glacial acetic acid before being added to the acid chloride. Solution was sonicated to mix before being allowed to react overnight at room temperature. Solvent was removed and crude product was purified on a 50 g C18 reversed-phase column (acetonitrile/water w/0.05% TFA). Product was isolated as a TFA salt (33% yield); $^1$H NMR (400 MHz, DMSO-$d_6$) δ 13.42 (s, 1H), 10.67 (s, 1H), 8.68 (m, 3H), 7.95 (dd, J=9.2, 2.4 Hz, 1H), 7.83 (d, J=9.2 Hz, 1H), 7.74 (s, 1H), 7.64 (m, 2H), 7.50 (m, 2H), 2.97 (s, 3H); LCMS: m/z calcd. for $C_{21}H_{16}ClN_3OS$ [M+H]$^+$: 394.07; found [M+H]$^+$: 394.0.

TABLE 1

| Compound Number | Structure | Observed m/z |
|---|---|---|
| 885 | 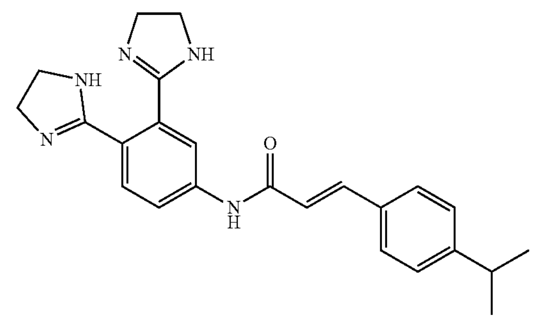 [SMILES: CC(C)c1ccc(/C=C/C(=O)Nc2ccc(C3=NCCN3)c(C3=NCCN3)c2)cc1] | 402.2 |
| 449 | 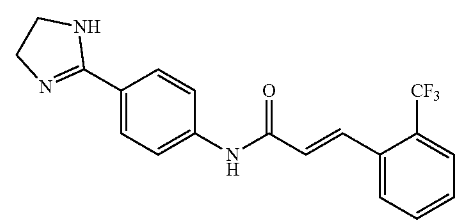 [SMILES: O=C(/C=C/c1ccccc1C(F)(F)F)Nc1ccc(C2=NCCN2)cc1] | 360.1 |
| 448 | 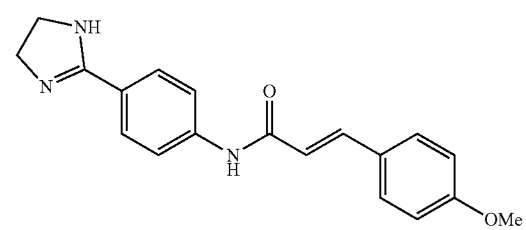 [SMILES: COc1ccc(/C=C/C(=O)Nc2ccc(C3=NCCN3)cc2)cc1] | 321.2 |
| 419 | 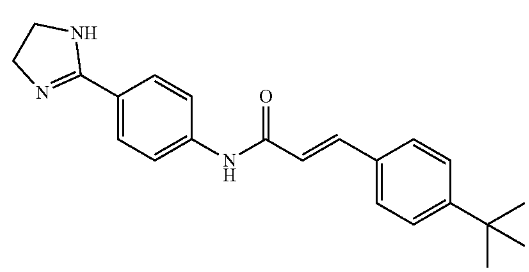 [SMILES: CC(C)(C)c1ccc(/C=C/C(=O)Nc2ccc(C3=NCCN3)cc2)cc1] | 360.1 |

Compounds of the Present Disclosure

TABLE 1-continued
| Compound Number | Structure | Observed m/z |
|---|---|---|
| 417 | 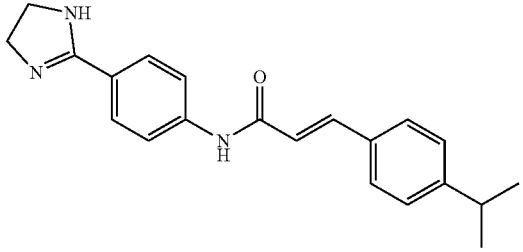 [SMILES: CC(C)c1ccc(/C=C/C(=O)Nc2ccc(C3=NCCN3)cc2)cc1] | 334.2 |
| 415 | 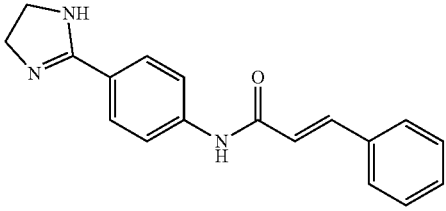 [SMILES: O=C(/C=C/c1ccccc1)Nc1ccc(C2=NCCN2)cc1] | 292.1 |
| 365 | 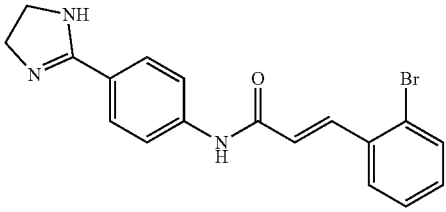 [SMILES: O=C(/C=C/c1ccccc1Br)Nc1ccc(C2=NCCN2)cc1] | 370.1 |
| 361 | 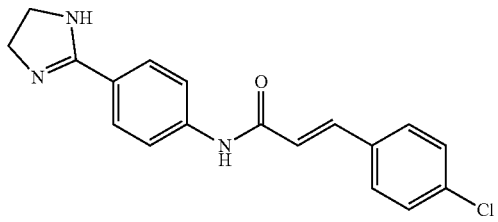 [SMILES: O=C(/C=C/c1ccc(Cl)cc1)Nc1ccc(C2=NCCN2)cc1] | 326.1 |
| 360 | 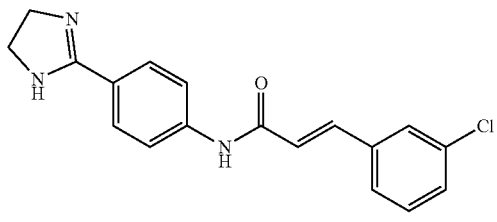 [SMILES: O=C(/C=C/c1cccc(Cl)c1)Nc1ccc(C2=NCCN2)cc1] | 326.1 |
| 225 | 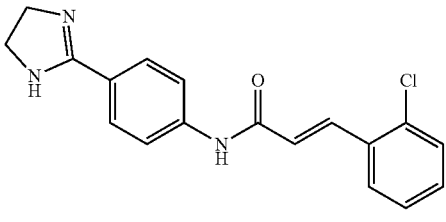 [SMILES: O=C(/C=C/c1ccccc1Cl)Nc1ccc(C2=NCCN2)cc1] | 326.1 |

TABLE 1-continued
Compounds of the Present Disclosure
| Compound Number | Structure | Observed m/z |
|---|---|---|
| 998 | 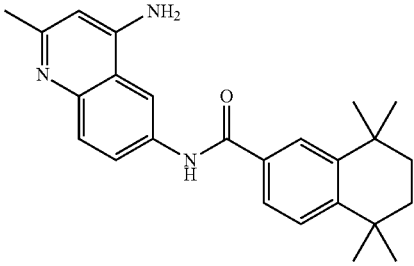 [SMILES: Cc1cc(N)c2cc(NC(=O)c3ccc4c(c3)C(C)(C)CCC4(C)C)ccc2n1] | 388.2 |
| 995 | 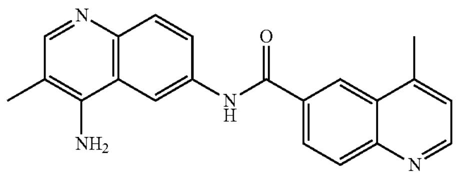 [SMILES: Cc1cnc2ccc(NC(=O)c3ccc4nccc(C)c4c3)cc2c1N] | 343.1 |
| 986 | 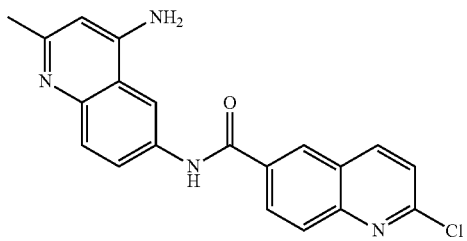 [SMILES: Cc1cc(N)c2cc(NC(=O)c3ccc4nc(Cl)ccc4c3)ccc2n1] | 363 |
| 884 | 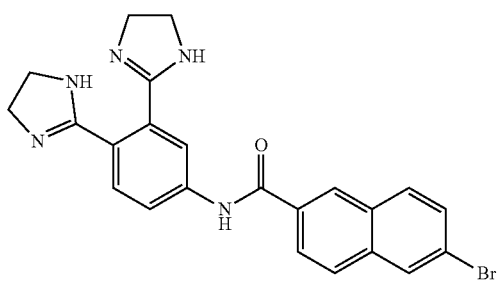 [SMILES: O=C(Nc1ccc(C2=NCCN2)c(C2=NCCN2)c1)c1ccc2cc(Br)ccc2c1] | 230.1, 234.9 |
| 843 | 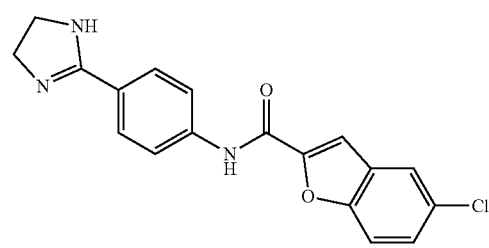 [SMILES: O=C(Nc1ccc(C2=NCCN2)cc1)c1cc2cc(Cl)ccc2o1] | 340.1 |
| 452 | 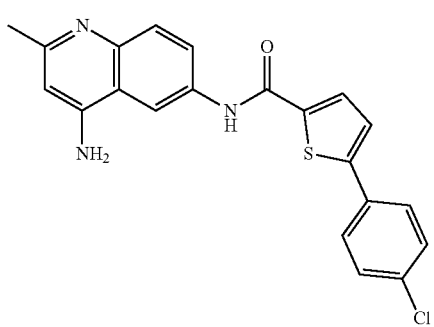 [SMILES: Cc1cc(N)c2cc(NC(=O)c3ccc(-c4ccc(Cl)cc4)s3)ccc2n1] | 394 |

TABLE 1-continued

Compounds of the Present Disclosure

| Compound Number | Structure | Observed m/z |
|---|---|---|
| 451 | 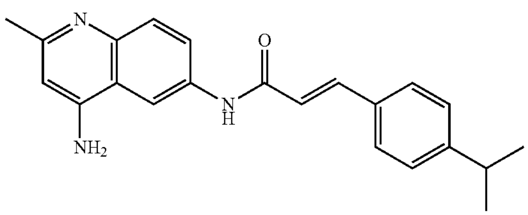 [SMILES: Cc1cc(N)c2cc(NC(=O)/C=C/c3ccc(C(C)C)cc3)ccc2n1] | 346.2 |
| 450 | 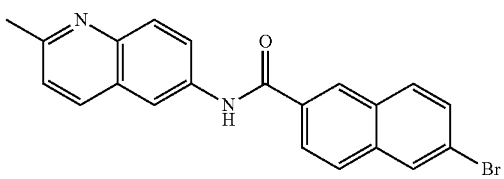 [SMILES: Cc1ccc2cc(NC(=O)c3ccc4cc(Br)ccc4c3)ccc2n1] | 391.0, 393.0 |
| 446 | 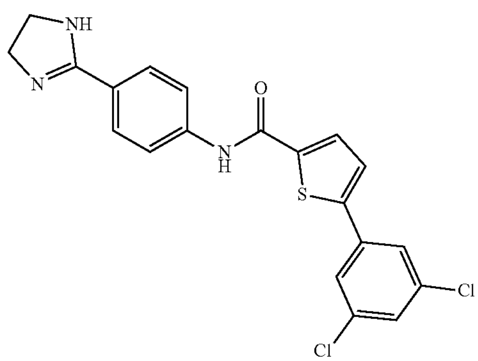 [SMILES: O=C(Nc1ccc(C2=NCCN2)cc1)c1ccc(-c2cc(Cl)cc(Cl)c2)s1] | 461 |
| 388 | 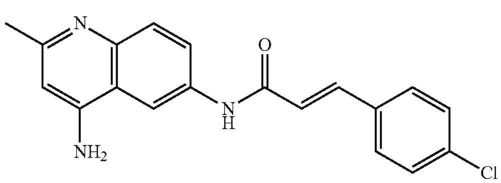 [SMILES: Cc1cc(N)c2cc(NC(=O)/C=C/c3ccc(Cl)cc3)ccc2n1] | 338 |

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods, and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VI. REFERENCES

Abdali et al., ACS Infect Dis, 3(1): p. 89-98, 2017.
Awoonor-Williams et al., Biochim Biophys Acta, 1858(7 Pt B): p. 1672-87, 2016.
Bush et al., Nat Rev Microbiol, 9(12): p. 894-6, 2011.
CA798859A
Cai et al., Anal Biochem, 385(2): p. 321-5, 2009.
Davis et al., ACS Chemical Biology, 9(11): p. 2535-2544, 2014.
Eicher et al., Proc Natl Acad Sci USA, 109(15): p. 5687-92, 2012.
Fange et al., Proceedings of the National Academy of Sciences, 106(20): p. 8215-8220, 2009.
Gamage et al., Bioorganic & Medicinal Chemistry, 21(11): p. 3147-3153, 2013.
Haynes et al., J Med Chem, 60(14): p. 6205-6219, 2017.
http://www.who.int/medicines/publications/WHO-PPL-Short_Summary_25Feb-ET_NM_WHO.pdf?ua=1.
Krishnamoorthy et al., Antimicrob Agents Chemother, 60(12): p. 7372-7381, 2016.
Krishnamoorthy et al., MBio, 8(5), 2017.
Lewis, Nature, 485(7399): p. 439-440, 2012.
Li et al., Antimicrob Agents Chemother, 47(1): p. 27-33, 2003.
Li et al., Journal of Antimicrobial Chemotherapy, 45(4): p. 433-6, 2000.

Livermore, Clin Microbiol Infect, 10 Suppl 4: p. 1-9, 2004.
Lomovskaya et al., Antimicrob Agents Chemother, 43(6): p. 1340-6, 1999.
Lomovskaya et al., Antimicrob Agents Chemother, 45(1): p. 105-16, 2001.
Lomovskaya et al., *Transporters as Drug Carriers*, Wiley and Sons. p. in press, 2008.
Lomovskaya, et al., Nat Rev Drug Discov, 6(1): p. 56-65, 2007.
Lovmar et al., The EMBO Journal, 28(6): p. 736-744, 2009.
Mohammad et al., J Biol Chem, 286(10): p. 8000-13, 2011.
Nakashima et al., Nature, 480(7378): p. 565-9, 2011.
Nikaido & Pages, FEMS Microbiol Rev, 36(2): p. 340-63, 2012.
Nikaido, Microbiol Mol Biol Rev, 67(4): p. 593-656, 2003.
Oethinger et al., Antimicrobial Agents & Chemotherapy, 44(1): p. 10-3, 2000.
Richmond et al., Journal of Antimicrobial Chemotherapy, 10.1093/jac/dkt052, 2013.
Richter et al., Nature, 10.1038/nature22308, 2017.
Ruggerone et al., Curr Top Med Chem, 13(24): p. 3079-100, 2013.
Silver, Bioorg Med Chem, 24(24): p. 6379-6389, 2016.
Silver, Clin Microbiol Rev, 24(1): p. 71-109, 2011.
Sjuts et al., Proc Natl Acad Sci USA, 113(13): p. 3509-14, 2016.
Vargiu et al., Antimicrob Agents Chemother, 58(10): p. 6224-34, 2014.
Westfall et al., PLoS One, 12(9): p. e0184671, 2009.
Zgurskaya et al., ACS Infect Dis, 1(11): p. 512-522, 2015.
Zgurskaya et al., Biochim Biophys Acta, 1794(5): p. 723-4, 2009.
Zgurskaya, Future Microbiol, 4(7): p. 919-32, 2009.

What is claimed:

1. A method of determining permeability of a cellular membrane comprising:
   (a) contacting a cell with a compound having the structure:

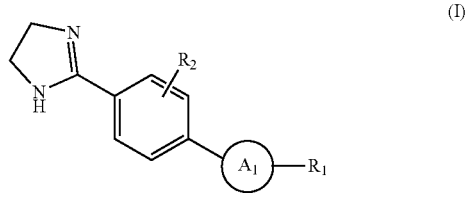

(I)

wherein:
   $A_1$ is arenediyl$_{(C \leq 12)}$, heteroarenediyl$_{(C \leq 12)}$, heterocycloalkanediyl$_{(C \leq 12)}$, or a substituted version of these groups, or $NR_3C(O)Y_1$—; wherein:
      $R_3$ is hydrogen, alkyl$_{(C \leq 6)}$, or substituted alkyl$_{(C \leq 6)}$;
      $Y_1$ is a covalent bond, alkanediyl$_{(C \leq 12)}$, alkenediyl$_{(C \leq 12)}$, arenediyl$_{(C \leq 12)}$, heteroarenediyl$_{(C \leq 12)}$, or a substituted version of any of these groups;
   $R_1$ is aryl$_{(C \leq 18)}$, substituted aryl$_{(C \leq 18)}$, heteroaryl$_{(C \leq 18)}$, or substituted heteroaryl$_{(C \leq 18)}$; and
   $R_2$ is hydrogen, amino, cyano, halo, hydroxy, or alkyl$_{(C \leq 8)}$, aryl$_{(C \leq 8)}$, aralkyl$_{(C \leq 8)}$, acyl$_{(C \leq 8)}$, alkoxy$_{(C \leq 8)}$, heteroaryl$_{(C \leq 12)}$, heterocycloalkyl$_{(C \leq 12)}$, alkylamino$_{(C \leq 8)}$, dialkylamino$_{(C \leq 8)}$, or a substituted version of any of these groups; or a compound of the formula:

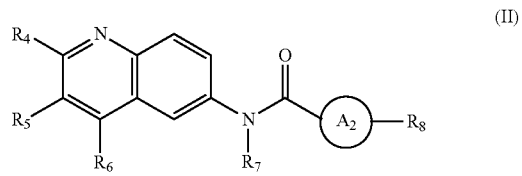

(II)

wherein:
   $A_2$ is covalent bond, alkenediyl$_{(C \leq 12)}$, or substituted alkenediyl$_{(C \leq 12)}$;
   $R_4$ and $R_5$ are each independently hydrogen, alkyl$_{(C \leq 8)}$, or substituted alkyl$_{(C \leq 8)}$;
   $R_6$ is hydrogen, hydroxy, or amino; or alkoxy$_{(C \leq 8)}$, acyloxy$_{(C \leq 8)}$, alkylamino$_{(C \leq 8)}$, dialkylamino$_{(C \leq 8)}$, or a substituted version of any of these groups;
   $R_7$ is hydrogen, alkyl$_{(C \leq 6)}$, or substituted alkyl$_{(C \leq 6)}$; and
   $R_8$ is aryl$_{(C \leq 18)}$, substituted aryl$_{(C \leq 18)}$, heteroaryl$_{(C \leq 18)}$, substituted heteroaryl$_{(C \leq 18)}$;

or a pharmaceutically acceptable salt thereof;

(b) incubating said cell for sufficient time to permit uptake of said compound by said cell;

(c) measuring a change fluorescent signal as compared to said cell prior to step (a), wherein the change in fluorescent signal is a measure of membrane permeability.

2. The method of claim 1, wherein the compound is further defined as:

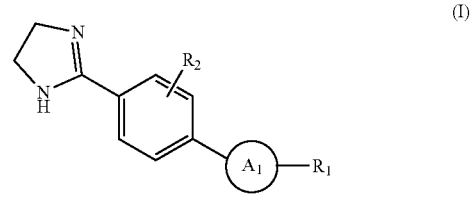

(I)

wherein:
   $A_1$ is arenediyl$_{(C \leq 12)}$, heteroarenediyl$_{(C \leq 12)}$, heterocycloalkanediyl$_{(C \leq 12)}$, or a substituted version of these groups, or —$NR_3C(O)Y_1$—; wherein:
      $R_3$ is hydrogen, alkyl$_{(C \leq 6)}$, or substituted alkyl$_{(C \leq 6)}$;
      $Y_1$ is a covalent bond, alkanediyl$_{(C \leq 12)}$, alkenediyl$_{(C \leq 12)}$, arenediyl$_{(C \leq 12)}$, heteroarenediyl$_{(C \leq 12)}$, or a substituted version of any of these groups;
   $R_1$ is aryl$_{(C \leq 18)}$, substituted aryl$_{(C \leq 18)}$, heteroaryl$_{(C \leq 18)}$, or substituted heteroaryl$_{(C \leq 18)}$; and
   $R_2$ is hydrogen, amino, cyano, halo, hydroxy, or alkyl$_{(C \leq 8)}$, aryl$_{(C \leq 8)}$, aralkyl$_{(C \leq 8)}$, acyl$_{(C \leq 8)}$, alkoxy$_{(C \leq 8)}$, heteroaryl$_{(C \leq 12)}$, heterocycloalkyl$_{(C \leq 12)}$, alkylamino$_{(C \leq 8)}$, dialkylamino$_{(C \leq 8)}$, or a substituted version of any of these groups;

or a pharmaceutically acceptable salt thereof.

3. The method of claim 1, wherein said compound is further defined as:

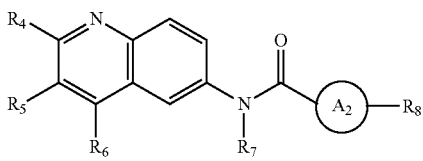

wherein:
- $A_2$ is covalent bond, alkenediyl$_{(C\leq12)}$, or substituted alkenediyl$_{(C\leq12)}$;
- $R_4$ and $R_5$ are each independently hydrogen, alkyl$_{(C\leq8)}$, or substituted alkyl$_{(C\leq8)}$;
- $R_6$ is hydrogen, hydroxy, or amino; or alkoxy$_{(C\leq8)}$, acyloxy$_{(C\leq8)}$, alkylamino$_{(C\leq8)}$, dialkylamino$_{(C\leq8)}$, or a substituted version of any of these groups;
- $R_7$ is hydrogen, alkyl$_{(C\leq6)}$, or substituted alkyl$_{(C\leq6)}$; and
- $R_8$ is aryl$_{(C\leq18)}$, substituted aryl$_{(C\leq18)}$, heteroaryl$_{(C\leq18)}$, substituted heteroaryl$_{(C\leq18)}$;

or a pharmaceutically acceptable salt thereof.

4. The method of claim 1, wherein said compound is further defined as:

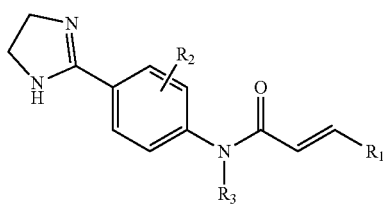

wherein:
- $R_1$ is aryl$_{(C\leq18)}$, substituted aryl$_{(C\leq18)}$, heteroaryl$_{(C\leq18)}$, or substituted heteroaryl$_{(C\leq18)}$;
- $R_2$ is hydrogen, amino, cyano, halo, hydroxy, or alkyl$_{(C\leq8)}$, aryl$_{(C\leq8)}$, aralkyl$_{(C\leq8)}$, acyl$_{(C\leq8)}$, alkoxy$_{(C\leq8)}$, alkylamino$_{(C\leq8)}$, dialkylamino$_{(C\leq8)}$, or a substituted version of any of these groups; and
- $R_3$ is hydrogen, alkyl$_{(C\leq6)}$, or substituted alkyl$_{(C\leq6)}$;

or a pharmaceutically acceptable salt thereof.

5. The method of claim 1, wherein $R_2$ is hydrogen.

6. The method of claim 1, wherein $R_3$ is hydrogen.

7. The method of claim 1, wherein the compound is further defined as:

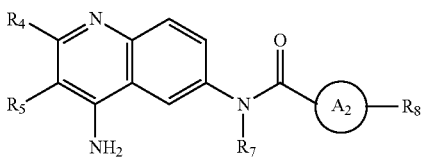

wherein:
- $A_2$ is covalent bond, alkenediyl$_{(C\leq12)}$, or substituted alkenediyl$_{(C\leq12)}$;
- $R_4$ and $R_5$ are each independently hydrogen, alkyl$_{(C\leq8)}$, or substituted alkyl$_{(C\leq8)}$;
- $R_7$ is hydrogen, alkyl$_{(C\leq6)}$, or substituted alkyl$_{(C\leq6)}$; and
- $R_8$ is aryl$_{(C\leq18)}$, substituted aryl$_{(C\leq18)}$, heteroaryl$_{(C\leq18)}$, substituted heteroaryl$_{(C\leq18)}$;

or a pharmaceutically acceptable salt thereof.

8. The method of claim 1, further comprising quantitating the change in fluorescent signal.

9. The method of claim 8, wherein the fluorescent signal is quantitated by fluorescence microscopy.

10. The method of claim 8, wherein the fluorescent signal is quantitated by fluorometer.

11. The method of claim 1, wherein said cell is a bacteria.

12. The method of claim 11, wherein said cell is a Gram-negative bacterial cell.

13. The method of claim 11, wherein said bacterial cell is *Escherichia coli, Pseudomonas aeruginosa, Acinetobacter baumannii, Klebsiella* species, *Enterobacter* species, *Burkholderia* species or *Stenotrophomonas maltophilia*.

14. The method of claim 11, wherein said bacterial cell is multi-drug resistant.

15. The method of claim 1, wherein said cell is a fungal cell.

16. The method of claim 15, wherein said fungal cell is a *Candida* species, *Saccharomyces* species, or *Aspergillus* species.

17. The method of claim 1, wherein said cell is a cancer cell.

18. The method of claim 1, further comprising performing steps (b)-(c) in the presence of a candidate substance suspected of having membrane permeabilization activity.

19. The method of claim 1, wherein step (c) is performed at multiple time points following step (b).

20. A method of determining efflux transport activity of a cellular membrane comprising:
(a) contacting a cell with a compound of the formula:

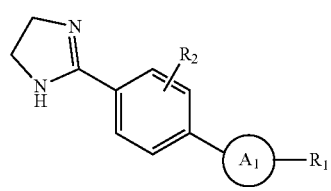

wherein:
- A is arenediyl$_{(C\leq12)}$, heteroarenediyl$_{(C\leq12)}$, heterocycloalkanediyl$_{(C\leq12)}$, or a substituted version of these groups, or —NR$_3$C(O)Y$_1$—; wherein:
  - $R_3$ is hydrogen, alkyl$_{(C\leq6)}$, or substituted alkyl$_{(C\leq6)}$;
  - $Y_1$ is a covalent bond, alkanediyl$_{(C\leq12)}$, alkenediyl$_{(C\leq12)}$, arenediyl$_{(C\leq12)}$, heteroarenediyl$_{(C\leq12)}$, or a substituted version of any of these groups;
- $R_1$ is aryl$_{(C\leq18)}$, substituted aryl$_{(C\leq18)}$, heteroaryl$_{(C\leq18)}$, or substituted heteroaryl$_{(C\leq18)}$; and
- $R_2$ is hydrogen, amino, cyano, halo, hydroxy, or alkyl$_{(C\leq8)}$, aryl$_{(C\leq8)}$, aralkyl$_{(C\leq8)}$, acyl$_{(C\leq8)}$, alkoxy$_{(C\leq8)}$, heteroaryl$_{(C\leq12)}$, heterocycloalkyl$_{(C\leq12)}$, alkylamino$_{(C\leq8)}$, dialkylamino$_{(C\leq8)}$, or a substituted version of any of these groups; or a compound of the formula:

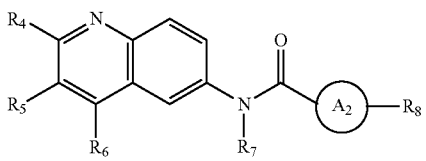

(II)

wherein:
- $A_2$ is covalent bond, alkenediyl$_{(C\leq12)}$, or substituted alkenediyl$_{(C\leq12)}$;
- $R_4$ and $R_5$ are each independently hydrogen, alkyl$_{(C\leq8)}$, or substituted alkyl$_{(C\leq8)}$;
- $R_6$ is hydrogen, hydroxy, or amino; or alkoxy$_{(C\leq8)}$, acyloxy$_{(C\leq8)}$, alkylamino$_{(C\leq8)}$, dialkylamino$_{(C\leq8)}$, or a substituted version of any of these groups;
- $R_7$ is hydrogen, alkyl$_{(C\leq6)}$, or substituted alkyl$_{(C\leq6)}$; and
- $R_8$ is aryl$_{(C\leq18)}$, substituted aryl$_{(C\leq18)}$, heteroaryl$_{(C\leq18)}$, substituted heteroaryl$_{(C\leq18)}$;

or a pharmaceutically acceptable salt thereof;
(b) incubating said cell for sufficient time to permit uptake of said compound by said cell;
(c) measuring a fluorescent signal in said cell; and
(d) measuring a change fluorescent signal in said cell as compared to step (c),
wherein the change in fluorescent signal is a measure of efflux transport activity.

21. A method of measuring cellular growth or inhibition of a cellular membrane comprising:
(a) contacting a cell with a compound of the formula:

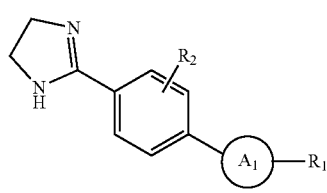

(I)

wherein:
- A is arenediyl$_{(C\leq12)}$, heteroarenediyl$_{(C\leq12)}$, heterocycloalkanediyl$_{(C\leq12)}$, or a substituted version of these groups, or —NR$_3$C(O)Y$_1$—; wherein:
  - $R_3$ is hydrogen, alkyl$_{(C\leq6)}$, or substituted alkyl$_{(C\leq6)}$;
  - $Y_1$ is a covalent bond, alkanediyl$_{(C\leq12)}$, alkenediyl$_{(C\leq12)}$, arenediyl$_{(C\leq12)}$, heteroarenediyl$_{(C\leq12)}$, or a substituted version of any of these groups;
- $R_1$ is aryl$_{(C\leq18)}$, substituted aryl$_{(C\leq18)}$, heteroaryl$_{(C\leq18)}$, or substituted heteroaryl$_{(C\leq18)}$; and
- $R_2$ is hydrogen, amino, cyano, halo, hydroxy, or alkyl$_{(C\leq8)}$, aryl$_{(C\leq8)}$, aralkyl$_{(C\leq8)}$, acyl$_{(C\leq8)}$, alkoxy$_{(C\leq8)}$, heteroaryl$_{(C\leq12)}$, heterocycloalkyl$_{(C\leq12)}$, alkylamino$_{(C\leq8)}$, dialkylamino$_{(C\leq8)}$, or a substituted version of any of these groups; or a compound of the formula:

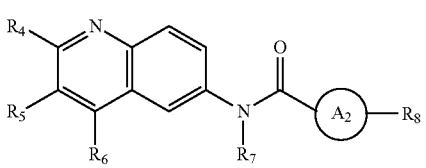

(II)

wherein:
- $A_2$ is covalent bond, alkenediyl$_{(C\leq12)}$, or substituted alkenediyl$_{(C\leq12)}$;
- $R_4$ and $R_5$ are each independently hydrogen, alkyl$_{(C\leq8)}$, or substituted alkyl$_{(C\leq8)}$;
- $R_6$ is hydrogen, hydroxy, or amino; or alkoxy$_{(C\leq8)}$, acyloxy$_{(C\leq8)}$, alkylamino$_{(C\leq8)}$, dialkylamino$_{(C\leq8)}$, or a substituted version of any of these groups;
- $R_7$ is hydrogen, alkyl$_{(C\leq6)}$, or substituted alkyl$_{(C\leq6)}$; and
- $R_8$ is aryl$_{(C\leq18)}$, substituted aryl$_{(C\leq18)}$, heteroaryl$_{(C\leq18)}$, substituted heteroaryl$_{(C\leq18)}$;

or a pharmaceutically acceptable salt thereof;
(b) incubating said cell for sufficient time to permit uptake of said compound by said cell;
(c) measuring a fluorescent signal in said cell; and
(d) measuring a change fluorescent signal in said cell as compared to step (c),
wherein the change in fluorescent signal is a measure of cellular growth or inhibition.

* * * * *